United States Patent
Liu et al.

(10) Patent No.: US 9,861,623 B1
(45) Date of Patent: Jan. 9, 2018

(54) COMBINATION TREATMENT OF RAS-POSITIVE DISEASES WITH PDE-δ INHIBITOR AND DIRECT AUTOPHAGY INHIBITOR

(71) Applicant: Macau University of Science and Technology, Taipa (MO)

(72) Inventors: Liang Liu, Taipa (MO); David Ward, Taipa (MO); Elaine Lai-Han Leung, Taipa (MO); Xiao Jun Yao, Taipa (MO); Vincent Kam-Wai Wong, Taipa (MO); Lian-Xiang Luo, Taipa (MO)

(73) Assignee: Macau University of Science and Technology, Taipa (MO)

( * ) Notice: Subject to any disclaimer, the term of this patent is extended or adjusted under 35 U.S.C. 154(b) by 0 days.

(21) Appl. No.: 15/337,293

(22) Filed: Oct. 28, 2016

(51) Int. Cl.
*A61K 31/454* (2006.01)
*A61K 31/52* (2006.01)

(52) U.S. Cl.
CPC ............ *A61K 31/454* (2013.01); *A61K 31/52* (2013.01)

(58) Field of Classification Search
None
See application file for complete search history.

(56) References Cited

PUBLICATIONS

Zimmermann et al., Nature (2013), 497(7451), pp. 638-642.*
Zimmermann et al., Journal of Medicinal Chemistry (2014), 57(12), pp. 5435-5448.*
Prior IA, Lewis PD, & Mattos C (2012) A comprehensive survey of Ras mutations in cancer. Cancer research 72 (10):2457-2467.
Spiegel J, Cromm PM, Zimmermann G, et al. (2014) Small-molecule modulation of Ras signaling. Nature chemical biology 10(8):613-622.
Acquaviva J, Smith DL, Sang J, et al. (2012) Targeting KRAS-mutant non-small cell lung cancer with the Hsp90 inhibitor ganetespib. Molecular cancer therapeutics 11(12):2633-2643.
Shaw RJ & Cantley LC (2006) Ras, PI(3)K and mTOR signalling controls tumour cell growth. Nature 441 (7092):424-430.
Sheridan C & Downward J (2013) Inhibiting the RAS-PI3K pathway in cancer therapy. The Enzymes 34 Pt. B:107-136.
Cox AD, Fesik SW, Kimmelman AC, et al. (2014) Drugging the undruggable RAS: Mission possible? Nature reviews. Drug discovery 13(11):828-851.
Lamba S, Russo M, Sun C, et al. (2014) RAF suppression synergizes with MEK inhibition in KRAS mutant cancer cells. Cell reports 8(5):1475-1483.
Xue W, Dahlman JE, Tammela T, et al. (2014) Small RNA combination therapy for lung cancer. Proceedings of the National Academy of Sciences of the United States of America 111(34):E3553-3561.
Papke B, Murarka S, Vogel HA, et al. (2016) Identification of pyrazolopyridazinones as PDEδ inhibitors. Nat Commun 7(11360):doi: 10.1038/ncomms11360.
Chandra A, Grecco HE, Pisupati V, et al. (2012) The GDI-like solubilizing factor PDEdelta sustains the spatial organization and signalling of Ras family proteins. Nature cell biology 14(2):148-158.
Zimmermann G, Schultz-Fademrecht C, Kuechler P, et al. (2014) Structure guided design and kinetic analysis of highly potent benzimidazole inhibitors targeting the PDEdelta prenyl binding site. Journal of medicinal chemistry 57 (12):5435-5448.
Zimmermann G, Papke B, Ismail S, et al. (2013) Small molecule inhibition of the KRAS-PDEdelta interaction impairs oncogenic KRAS signalling. Nature 497(7451):638-642.
DeNicola GM, Karreth FA, Humpton TJ, et al. (2011) Oncogene-induced Nrf2 transcription promotes ROS detoxification and tumorigenesis. Nature 475(7354):106-109.
Leung EL, Fan XX, Wong MP, et al. (2016) Targeting Tyrosine Kinase Inhibitor-Resistant Non-Small Cell Lung Cancer by Inducing Epidermal Growth Factor Receptor Degradation via Methionine 790 Oxidation. Antioxidants & redox signaling 24(5):263-279.
Chen N, Wu L, Yuan H, & Wang J (2015) ROS/Autophagy/Nrf2 Pathway Mediated Low-Dose Radiation Induced Radio-Resistance in Human Lung Adenocarcinoma A549 Cell. International journal of biological sciences 11 (7):833-844.
Franken NA, Rodermond HM, Stap J, Haveman J, & van Bree C (2006) Clonogenic assay of cells in vitro. Nature protocols 1(5):2315-2319.

* cited by examiner

*Primary Examiner* — Brian J Davis
(74) *Attorney, Agent, or Firm* — Renner Kenner Greive Bobak Taylor & Weber

(57) ABSTRACT

The present invention provides methods for treatment of a RAS-positive disease, in particular KRAS-positive non-small cell lung cancer as well as a method for potentiating the apoptotic activity of a PDEδ inhibitor by combining the PDEδ inhibitor with a direct autophagy inhibitor. The PDEδ inhibitor is preferably, but not exclusively, deltarasin, and the direct autophagy inhibitor is in particular 3-methyladenine. Further provided by the present invention are a kit and a pharmaceutical composition comprising the PDEδ inhibitor and a direct autophagy inhibitor. The methods of the present invention in particular provide a new treatment option for RAS-positive diseases such as KRAS-positive non-small cell lung cancer allowing for an increased apoptotic activity of the PDEδ inhibitor by simultaneously blocking its "tumor protective" autophagy.

20 Claims, 27 Drawing Sheets

COMBINATION TREATMENT OF RAS-POSITIVE DISEASES WITH PDE-δ INHIBITOR AND DIRECT AUTOPHAGY INHIBITOR

TECHNICAL FIELD

The present invention relates to methods for treatment of a RAS-positive disease, in particular KRAS-positive non-small cell lung cancer as well as to a method of potentiating the apoptotic activity of a PDEδ inhibitor by combining the PDEδ inhibitor with a direct autophagy inhibitor. The PDEδ inhibitor is especially preferably but not exclusively deltarasin and the direct autophagy inhibitor is in particular 3-methyladenine. Further provided by the present invention are a kit and a pharmaceutical composition comprising the PDEδ inhibitor and the direct autophagy inhibitor.

BACKGROUND OF THE INVENTION

RAS proto-oncogene encoded oncoproteins, i.e. the RAS family, represent small guanosine triphosphate (GTP)-binding proteins acting as molecular switches by alternating between an active GTP-bound and an inactive GDP-bound form. RAS proteins are central mediators downstream of growth factor receptor signaling and therefore are critical for controlling cell proliferation, differentiation and apoptosis. RAS can activate several downstream effectors, including the PI3K-Akt-mTOR pathway and the Ras-Raf-MEK-ERK pathway.

Approximately 20% to 30% of all human cancers harbor RAS oncogenic mutations, making RAS variants to highly relevant drivers of cancer. Three different RAS protein isoforms and encoding genes have been identified so far. Of the three RAS isoforms, HRAS (homologous to the oncogene from the Harvey rat sarcoma virus), NRAS (first isolated from a human neuroblastoma), and KRAS (homologous to the oncogene from the Kirsten rat sarcoma virus) including splice variants like K-Ras4A and K-Ras4B, KRAS is the most frequently mutated RAS isoform (86%) and is commonly found in more than 30% of all lung adenocarcinomas. Moreover, hyperactive RAS such as hyperactive KRAS signaling contributes to common immunological and inflammatory disorders, such as rheumatoid arthritis and diabetes. Inhibiting KRAS signaling has been considered for being a mission impossible in the past. Thus, there is a strong need for new effective strategies for inhibiting hyperactive RAS such as hyperactive KRAS signaling.

Mutations of the KRAS gene are usually characterized by a single base missense mutation, which is predominantly found at codons G12, G13 or Q61 residues leading to a constitutive activation of KRAS (Prior, I. A. et al., Cancer research, 2012, 72(10):2457-2467). Constitutive activation of KRAS leads to the persistent stimulation of downstream signaling pathways that promote tumorigenesis (Spiegel, J. et al., Nature chemical biology, 2014, 10(8):613-622, Acquaviva, J., et al. Molecular cancer therapeutics, 2012, 11(12):2633-2643, Shaw, R. J. and Cantley, L. C. Nature, 2006, 441(7092):424-430, Sheridan, C. and Downward, J. The Enzymes, 2013, 34 Pt. B:107-136). Efforts have been made for over three decades to develop effective RAS inhibitors, however no pharmacological inhibitor of the RAS oncoprotein has as yet led to a clinically useful drug (Cox, A. D., Drug discovery, 2014, 13(11):828-851).

Numerous strategies, including blocking RAS membrane associations, RAS siRNA technology, targeting RAS downstream effector signaling, inhibiting synthetic lethal interactors with mutant RAS, and suppressing cell metabolism are currently being evaluated in preclinical or clinical studies (Cox, A. D., Drug discovery, 2014, 13(11):828-851, Ostrem, J. M. and Shokat, K. M. Nature reviews. Drugdiscovery. 2016, Lamba, S., et al. Cell reports, 2014, 8(5):1475-1483, Xue, W., et al. Proceedings of the National Academy of Sciences of the United States of America, 2014, 111(34): E3553-3561, Papke, B. Nat Commun, 2016, 7(11360):doi: 10.1038/ncomms11360).

The recent elucidation of the crystalline structure of the cGMP phosphodiesterase (PDEδ) protein and the identification of deltarasin, a molecule that inhibits the binding of PDEδ to activated RAS proteins, has provided hopes in the development of anti-RAS therapy (Chandra, A., et al. Nature cell biology, 2012, 14(2):148-158). Initially, when RAS protein is in the inactive state, it undergoes a rapid series of complex post-translational modifications, which ensures it is capable of binding to the plasma membrane. PDEδ is now regarded as an important chaperone of prenylated small G proteins and a prenyl-binding protein of the RAS superfamily, which can bind to RAS protein and recruit it to the plasma membrane. In particular, PDEδ contains a deep hydrophobic pocket, capable of binding the lipid moiety of farnesyl-acylated proteins such as RAS. Therefore, inhibiting the interaction between RAS-PDEδ could bear a potential therapeutic value.

Deltarasin has been found to bind to the farnesyl-binding pocket of His-tagged PDEδ and to disrupt binding to a biotinylated and farnesylated KRAS peptide (Zimmermann, G., et al., Nature, 2013, 497(7451):638-642). Fluorescence lifetime imaging microscopy (FLIM)-based fluorescence resonance energy transfer (FRET) assays showed that deltarasin inhibits the interaction between KRAS-PDEδ and decreases KRAS binding to the plasma membrane in human ductal adenocarcinoma (PDAC) cell lines harboring KRAS gene mutations, resulting in a reduction of cell proliferation and an induction of apoptosis both in vitro and in vivo. Although the discovery of deltarasin is promising for making the KRAS signaling pathway targetable, the ability of deltarasin to treat other clinical diseases than pancreatic cancer associated with RAS abnormalities, such as suppress lung cancer growth and the factors affecting deltarasin sensitivity have not yet been explored.

Accordingly, there remains a strong need for therapeutic approaches for treating diseases with hyperactive RAS signaling such as hyperactive KRAS signaling, in particular cancer such as non-small cell lung cancer as a leading cause of cancer death and most common type of lung cancer.

SUMMARY OF THE INVENTION

The first aspect of the present invention relates to a method of treating a subject suffering from a RAS-positive disease, in particular a RAS-positive cancer such as KRAS-positive non-small cell lung cancer (NSCLC). Said method comprises administering an effective amount of a combination of:

(i) a PDEδ inhibitor having a structure of Formula (I),

Formula (I)

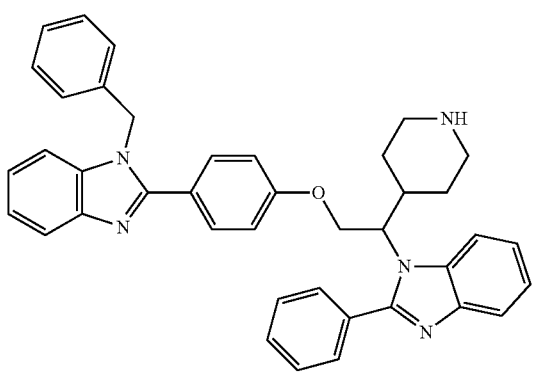

and
(ii) a direct autophagy inhibitor
to the subject, in particular a mammal such as a human.

The RAS-positive disease such as the KRAS-positive cancer is in particular associated with at least one RAS gene mutation, i.e. with an expression of at least one RAS mutant protein, in particular an expression of a RAS mutant protein with enhanced activity compared to the wild-type RAS protein.

In particular embodiments of the method of the present invention, the PDEδ inhibitor is deltarasin having a structure of Formula (Ia):

Formula (Ia)

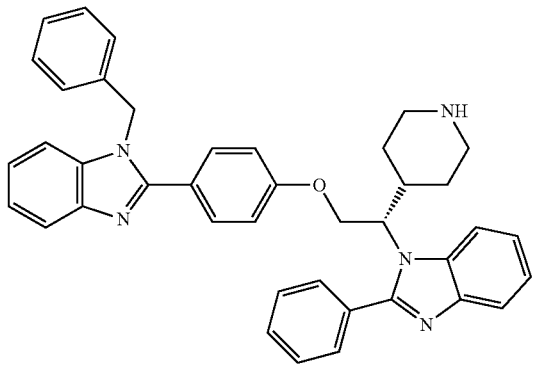

and the direct autophagy inhibitor is 3-methyladenine having a structure of Formula (II):

Formula (II)

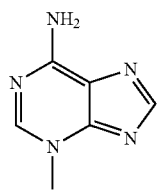

Further provided with the present invention is a method of potentiating the apoptotic activity of a PDEδ inhibitor in RAS-positive cells such as from a RAS-positive cancer like KRAS-positive NSCLC adenocarcinoma comprising contacting the cells with:
(i) a PDEδ inhibitor having a structure of Formula (I), and
(ii) a direct autophagy inhibitor.

In particular, the direct autophagy inhibitor inhibits the autophagic activity of the PDEδ inhibitor.

The direct autophagy inhibitor can increase the percentage of apoptotic cells and the cleavage of poly (ADP-ribose) polymerase (PARP) and/or the reactive oxygen species production as present under the PDEδ inhibitor, i.e. as present when the cells are contacted with the same concentration of the PDEδ inhibitor without the direct autophagy inhibitor.

In particular, the PDEδ inhibitor is deltarasin having a structure of Formula (Ia) and the direct autophagy inhibitor is 3-methyladenine having a structure of Formula (II).

In a further aspect, the present invention provides a method of treating a subject suffering from a RAS-positive lung cancer, in particular KRAS-positive NSCLC like KRAS-positive NSCLC adenocarcinoma, comprising administering an effective amount of a composition such as a pharmaceutical composition comprising a PDEδ inhibitor having a structure of Formula (I) to the subject.

The administration of the effective dose of the composition such as pharmaceutical composition comprising the PDEδ inhibitor in particular induces apoptosis in the cancer cells by inhibiting the interaction of KRAS with PDEδ.

The composition such as the pharmaceutical composition in particular further comprises a direct autophagy inhibitor. Said direct autophagy inhibitor in particular inhibits the autophagy induced by the PDEδ inhibitor and potentiates the apoptotic activity of the PDEδ inhibitor.

The PDEδ inhibitor is in particular deltarasin having a structure of Formula (Ia) and the pharmaceutical composition further comprises a direct autophagy inhibitor, which is 3-methyladenine having a structure of Formula (II).

In another aspect, the present invention refers to a kit comprising an effective dose of:
(i) a PDEδ inhibitor having a structure of Formula (I), and
(ii) a direct autophagy inhibitor.

The PDEδ inhibitor is in particular deltarasin having a structure of Formula (Ia) and the direct autophagy inhibitor is preferably 3-methyladenine having a structure of Formula (II).

Further provided by the present invention is a pharmaceutical composition comprising:
(i) a PDEδ inhibitor having a structure of Formula (I), in particular of Formula (Ia), and
(ii) a direct autophagy inhibitor, in particular of Formula (II), and
(iii) at least one pharmaceutically acceptable excipient selected from one or more of a carrier, a salt, a buffer, water, a diluent, a filler, a binder, a disintegrant, a lubricant, a coloring agent, a surfactant and a preservative or a combination thereof.

According to the invention is also a PDEδ inhibitor, in particular of Formula (Ia), for use as a medicament for the treatment of KRAS-positive NSCLC, wherein the PDEδ inhibitor is used in combination with a direct autophagy inhibitor, in particular of Formula (II). Another aspect of the present invention refers to the use of the PDEδ inhibitor, in particular of Formula (Ia), for preparing a medicament for use for the treatment of KRAS-positive NSCLC, wherein the PDEδ inhibitor is used in combination with a direct autophagy inhibitor, in particular of Formula (II). The present invention also relates to the use of a combination of a PDEδ inhibitor, in particular of Formula (Ia), and a direct autophagy inhibitor, in particular of Formula (II), for inducing apoptosis, in particular for increasing the percentage of apoptotic cells, the cleavage of PARP and the ROS production.

The methods of the present invention allow for treating RAS-positive such as KRAS-positive diseases, in particular RAS-positive cancer like NSCLC and, thus, provide a highly promising treatment option for such diseases.

The inventors in particular found that the PDEδ inhibitor deltarasin is able to inhibit the growth of NSCLC cell lines A549 and H358 harboring KRAS mutations, producing both apoptosis and autophagy. They in particular demonstrated that deltarasin inhibits the interaction of RAS with PDEδ as well as the downstream Raf/MEK/ERK, PI3K/Akt signaling pathways in NSCLC cells harboring a KRAS mutation. Moreover, they found that deltarasin also suppresses colony formation and lung cancer cell growth in NSCLC cells harboring a KRAS mutation. In addition, they could show for the first time that deltarasin can increase intracellular ROS levels and induce autophagy in KRAS-positive NSCLC cells.

They unexpectedly found that autophagy plays a protective role in the process which weakens the overall anti-cancer effect of deltarasin and that blocking autophagy can sensitize cells to deltarasin treatment. This was surprising as autophagy is known for being a kind of double-edged sword, namely it acts both as tumor suppressor and tumor protector of cell survival and its role in cancer is complex and controversial. In particular, the inventors could show that when combining the PDEδ inhibitor of Formula (I) with a direct autophagy inhibitor, the apoptotic activity of said PDEδ inhibitor can be markedly increased such as via elevation of ROS. In particular, the inventors could show a significant increase in the percentage of apoptotic cells, a significant increase in the cleavage of PARP, a significant increase in the production of ROS under the PDEδ inhibitor deltarasin accompanied by a reduced autophagic activity of said PDEδ inhibitor when a combination of deltarasin with the direct autophagy inhibitor 3-methyladenine was used. Such increase in apoptotic activity of the PDEδ inhibitor deltarasin could not be achieved when applying a combination of deltarasin and an antioxidant. In contrast, the inventors unexpectedly found that an inhibition of ROS by N-acetyl cysteine (NAC) significantly attenuates deltarasin-induced cell death. This was surprising, too, as ROS have been proposed to both promote and delay cancer cell initiation and expansion by complex and multiple mechanisms.

Collectively, a new and highly promising treatment option for RAS-positive diseases such as NSCLC with increased anti-cancer activity of a PDEδ inhibitor is provided by simultaneously blocking its "tumor protective" autophagy.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 1A to 1C show the cell viability in relation to the concentration of deltarasin in PANC-1, A549 and H358 cells treated with deltarasin (0, 0.6125, 1.25, 2.5, 5 and 10 μM) for 72 h. The percentage of cell viability was measured by MTT assay. FIG. 1A refers to the cell viability of PANC-1 cells. FIG. 1B refers to the cell viability of A549 cells. FIG. 1C refers to the cell viability of H358 cells. FIG. 1D to 1F show Western Blots with the levels of p-cRaf, cRaf, p-Akt, Akt, p-ERK, ERK and GAPDH of PANC-1, A549 and H358 cells after 24 h deltarasin treatment (0, 1.25, 2.5 and 5 μM). FIG. 1D refers to the results obtained with PANC-1 cells. FIG. 1E refers to the results obtained with A549 cells. FIG. 1F refers to the results obtained with H358 cells. Data are expressed as mean±SEM of three independent experiments (each in triplicate). ***P<0.001 when compared with control.

FIG. 2A to 2D show the morphological changes after 24 h exposure to deltarasin (0, 1.25, 2.5 and 5 μM) captured by an optical microscope with 100-fold magnification. FIG. 2A shows the control group without deltarasin treatment. FIG. 2B shows the cells after treatment with 1.25 μM deltarasin. FIG. 2C shows the cells after treatment with 2.5 μM deltarasin. FIG. 2D shows the cells after treatment with 5 μM deltarasin. FIG. 2E to 2G refer to the apoptosis under deltarasin treatment. A549 cells were treated with 5 μM deltarasin for 24 h and apoptosis levels were quantitatively measured with flow cytometry after staining the cells with Annexin V/propidium Iodide (P1); triplicate data were plotted as bar chart diagram. FIG. 2E is a flow cytometry pattern of the control group without deltarasin treatment. FIG. 2F is a flow cytometry pattern of the group with deltarasin treatment. FIG. 2G is a bar chart showing the percentage of apoptotic cells in the control group and under deltarasin treatment. FIG. 2H is a Western blot of apoptosis-related proteins (PARP, Bcl-2 and Bax) confirming induction of cellular apoptosis after deltarasin treatment (0, 1.25, 2.5 and 5 μM) for 24 h. All data are representative of at least three independent experiments, ***P<0.001 compared with control.

FIG. 3A to 3B show the KRAS GTP levels determined by incubating the protein lysates from A549 cells treated 5 μM deltarasin for 24 h with glutathione S-transferase (GST)-tagged RAS binding domain (RBD) immobilized on glutathione beads. FIG. 3A is a Western Blot showing the levels of GTP-RAS and total RAS. FIG. 3B is a bar chart showing the percentage of KRAS-GTP binding compared with untreated control. FIGS. 3C and 3D show the cellular localization of KRAS observed with fluorescence microscopy after 5 μM deltarasin treatment for 24 h (immunofluorescence signal of primary antibody against KRAS; Hoechst staining on cell nucleus. Magnification: 40×). FIG. 3C refers to the untreated control group. FIG. 3D refers to the deltarasin treatment group. FIG. 3E to 3I show the colony formation of A549 cells after deltarasin treatment (0, 1.25, 2.5 and 5 μM) for 10 days. Colony numbers were plotted and photographs of violet-stained colonies are shown. FIG. 3E shows the control group without deltarasin treatment. FIG. 3F shows the cells treated with 1.25 μM deltarasin. FIG. 3G shows the cells treated with 2.5 μM deltarasin. FIG. 3H shows the cells treated with 5 μM deltarasin. FIG. 3I is a bar chart showing the average colony number depending on the concentration of deltarasin treatment. The results are expressed as the mean±SEM of three independent experiments, *P<0.05; P<0.01; *P<0.001 vs control.

FIG. 4A to 4C are Western blots of the levels of LC3-I and LC3-II in PANC-1, A549 and H358 cells treated with deltarasin (0, 1.25, 2.5, 5 μM) for 24 h. FIG. 4A shows the levels in PANC-1 cells. FIG. 4B shows the levels in A549 cells. FIG. 4C shows the levels in H358 cells. FIG. 4D to 4F are Western blots of the levels of LC3-I and LC3-II in PANC-1, A549 and H358 cells treated with vehicle, 5 μM deltarasin, 5 mM 3-MA or a combination of both deltarasin and 3-MA for 24 h. FIG. 4D shows the levels in PANC-1 cells. FIG. 4E shows the levels in A549 cells. FIG. 4F shows the levels in H358 cells. FIG. 4G to 4K refer to the GFP-LC3 puncta formation in A549 cells transfected with GFP-LC3 plasmid for 24 h, and then treated with vehicle, 5 μM deltarasin, 5 mM 3-MA or in combination of both for 24 h. After treatment, deltarasin-induced autophagy manifesting as fluorescence green GFP-LC3 puncta assessed by fluorescence microscopy, magnification: 40×. FIG. 4G shows the untreated control group. FIG. 4H shows the group treated with deltarasin. FIG. 4I shows the group treated with 3-MA. FIG. 4J shows the group treated with deltarasin and 3-MA. FIG. 4K is a bar chart showing the percentage of cells with increased GFP-LC3 puncta formation. The results are expressed as the mean±SEM of three independent experiments, ***P<0.001 vs. control; *P<0.05 vs. deltarasin-treated alone group.

FIG. 5A is a Western Blot of the levels of p-mTOR, mTOR, p-p70s6k, p70s6k, p-AMPK, AMPK and GAPDH of A549 cells treated with 0, 1.25, 2.5, and 5 μM deltarasin for 24 h. FIG. 5B is a Western Blot of the levels of LC3-I and LC3-II of A549 cells treated with vehicle, 5 μM deltarasin, 5 μM Compound C or a combination of both for 24 h. FIG. 5C is a bar chart showing the relative level of LC3-II analyzed by Western blot with densitometry. The results are expressed as the mean±SEM of three independent experiments. *P<0.001 when compared with control and P<0.01 when compared with the deltarasin-treated alone group.

FIG. 6A shows flow cytometry patterns of A549 and H358 cells treated with vehicle, 5 μM deltarasin, 5 mM 3-MA or a combination of both for 24 h. Cell apoptosis was measured by Annexin V/PI double staining with flow cytometry. FIG. 6B is a bar-chart diagram showing the level of apoptosis of three representative experiments with A549 cells. FIG. 6C is a bar-chart diagram showing the level of apoptosis of three representative experiments with H358 cells. FIGS. 6D and 6E refer to A549 cells treated with vehicle, 5 μM deltarasin, 5 mM 3-MA or a combination of both for 24 h, wherein the level of PARP has been determined. FIG. 6D is a Western blot showing the levels of PARP under the different treatment conditions. FIG. 6E is a bar-chart diagram showing the densitometry quantitative analysis of three representative Western blots. FIGS. 6F and 6G refer to A549 cells treated with 5 μM deltarasin, 5 mM 3-MA or a combination of both for 24 h. ROS generation was measured by flow cytometry after DCF-DA staining. FIG. 6F shows the flow cytometry patterns obtained. FIG. 6G is a bar-chart diagram showing the percentage of cells with ROS generation. The results are expressed as the mean±SEM of three independent experiments, P<0.01 when compared with control and *P<0.001 or *P<0.05 when compared with the deltarasin-treated alone group.

FIG. 7A refers to PANC-1, A549 and H358 cells treated with vehicle, 5 μM deltarasin, 5 μM NAC or a combination of both for 24 h, then cells were stained with DCF-DA and the level of ROS was analyzed by flow cytometry. FIG. 7A shows the flow cytometry patterns obtained. FIG. 7B is a bar-chart diagram showing the percentage of cells with ROS generation in PANC-1 cells. FIG. 7C is a bar-chart diagram showing the percentage of cells with ROS generation in A549 cells. FIG. 7D is a bar-chart diagram showing the percentage of cells with ROS generation in H358 cells. FIG. 7E is a Western blot pattern, wherein A549 cells were treated with vehicle, 5 μM deltarasin, 5 μM NAC or a combination of both for 24 h. The levels of PARP cleavage and LC3 were evaluated. FIG. 7F is a bar-chart diagram showing the cell viability of A549 cells treated with vehicle, 5 μM deltarasin, 5 μM NAC or a combination of both for 24 h. The percentage of cell viability was measured by MTT assays. FIGS. 7G and 7H refer to A549 cells treated with vehicle, 5 μM deltarasin, 5 μM NAC or in combination of both for 24 h. The level of cell apoptosis was measured by Annexin V/PI double staining with flow cytometry. FIG. 7G shows flow cytometry patterns obtained. FIG. 7H is a bar-chart diagram showing the cell apoptosis. The results are expressed as the mean±SEM of three independent experiments, *P<0.05, P<0.01, *P<0.001, when compared with control or deltarasin-treated alone group.

DETAILED DESCRIPTION OF THE INVENTION

Figure 1A:
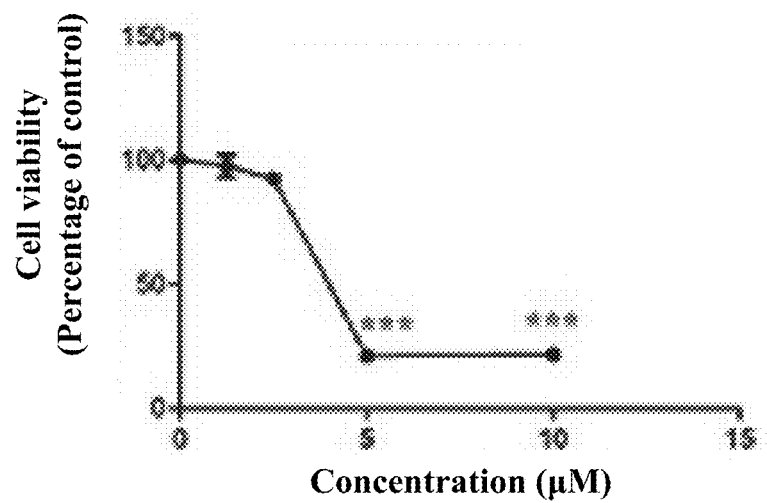
FIGS. 1A through 1F illustrate the effects of deltarasin on cell viability and KRAS signalling in both pancreatic and lung cancer cells.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention provides a method of treating a subject suffering from a RAS-positive disease. Said method comprises administering an effective amount of a combination of:

(i) a PDEδ inhibitor having a structure of Formula (I),

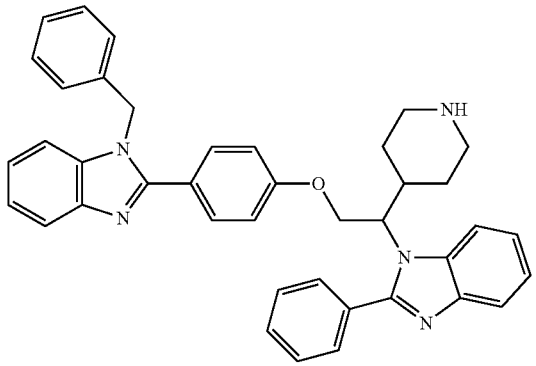

Formula (I)

and
(ii) a direct autophagy inhibitor
to the subject.

A RAS-positive disease is a disease accompanied by an enhanced expression or enhanced activity of a RAS protein compared to healthy subjects and healthy cells, respectively, in particular a hyperactive RAS signaling significantly exceeding the RAS signaling in healthy subjects and healthy cells. Preferably, the RAS-positive disease is a KRAS-positive disease, i.e. accompanied by an enhanced expression or enhanced activity of a KRAS protein compared to healthy subjects and healthy cells. In particular, the disease is a RAS-positive cancer, more preferably a KRAS-positive cancer.

More specifically, a "RAS-positive cancer", in particular a "KRAS-positive cancer", as used herein refers to a cancer or cancer cells having an enhanced expression or enhanced activity of a RAS protein such as KRAS protein. This can be assessed by the activation of one or more downstream pathways to RAS such as to KRAS. "Enhanced expression" or "enhanced activity" preferably means an increase in RAS protein expression or RAS protein activity by at least 5% compared to a reference control, i.e. normal (healthy) cells, i.e. non-cancerous cells. In particular, the RAS protein is a RAS mutant protein, in particular a KRAS mutant protein. The skilled person is able to determine the level of the expression of RAS such as KRAS and/or the RAS such as KRAS protein activity with common methods, for example, with well-known immunological assays that utilize antibody methods, Northern blotting, in-situ hybridization or similar techniques or qRT-PCR, RAS Activation Kits for determining the active form of RAS or by measuring the level of downstream effectors of the signaling pathway downstream to RAS.

In particular, said enhanced expression or enhanced activity of the RAS protein is highly correlated with the growth of the cancer.

The RAS-positive cancer such as the KRAS-positive cancer is in particular associated with at least one RAS gene mutation such as a KRAS gene mutation, i.e. with an expression of at least one RAS mutant protein, in particular an expression of a RAS mutant protein with enhanced activity compared to the wild-type RAS protein.

Namely, the RAS-positive cancer has cancer cells which preferably harbor at least one "RAS gene mutation", i.e. at least one mutation such as translocation or transversion in the RAS protein encoding genes, i.e. in the respective nucleotide sequences, which in particular results in an enhanced activity of RAS. The expressed "RAS mutant protein" in particular distinguishes from the wild-type RAS protein in the sequence of amino acids, especially at least one, in particular one amino acid has been replaced, also named substitution variant. "Wild type RAS protein" refers to a RAS protein with the sequence as present or encoded in normal (healthy) cells or tissue, namely non-cancerous cells or tissue without translocation or transversion in the RAS protein encoding genes.

The RAS gene mutation is in particular accompanied by an aberrant function of the expressed RAS mutant protein with a resulting upregulation of signaling pathways downstream to the RAS protein thereby stimulating cell proliferation and inhibiting apoptosis and leading to uncontrolled cell growth.

Preferably, the at least one RAS gene mutation concerns codons 12, 13 and/or 61 of the RAS protein encoding genes, more preferably, codon 12. In particular, the at least one RAS gene mutation is a KRAS gene mutation at codons 12 and/or 13 in exon 2 and/or 61 in exon 3 of the KRAS protein encoding gene, in particular at codons 12 or 13 in exon 2 or 61 in exon 3.

In particular, the KRAS gene mutation is a transversion mutation, i.e. a pyrimidine base is replaced with a purine base or vice versa, i.e. the KRAS is accompanied by an amino acid substitution in the respective expressed protein. The mutation is preferably accompanied by a replacement of amino acids G12, G13 and/or Q61 in the active site of the KRAS protein. I.e. the expressed KRAS mutant protein, is preferably a protein which distinguishes from the KRAS wild-type protein with regard to one or more of amino acids G12, G13 and/or Q61.

In particular, the KRAS gene mutation in the KRAS protein encoding gene at codon 12 is selected from:
  G12C (results in an amino acid substitution at position 12 in KRAS protein, from a glycine (G) to a cysteine (C));
  G12R (results in an amino acid substitution at position 12 in KRAS, from a glycine (G) to an arginine (R));
  G12S (results in an amino acid substitution at position 12 in KRAS, from a glycine (G) to a serine (S));
  G12A (results in an amino acid substitution at position 12 in KRAS, from a glycine (G) to an alanine (A));
  G12D (results in an amino acid substitution at position 12 in KRAS, from a glycine (G) to an aspartic acid (D)); and/or
  G12V (results in an amino acid substitution at position 12 in KRAS, from a glycine (G) to a valine (V)).

The KRAS gene mutation in the KRAS protein encoding gene at codon 13 is preferably selected from:
  G13C (results in an amino acid substitution at position 13 in KRAS, from a glycine (G) to a cysteine (C));
  G13R (results in an amino acid substitution at position 13 in KRAS, from a glycine (G) to an arginine (R));
  G13S (results in an amino acid substitution at position 13 in KRAS, from a glycine (G) to a serine (S));
  G13A (results in an amino acid substitution at position 13 in KRAS, from a glycine (G) to an alanine (A)); and/or
  G13D (results in an amino acid substitution at position 13 in KRAS, from a glycine (G) to an aspartic acid (D)).

The KRAS gene mutation in the KRAS protein encoding genes at codon 61 is preferably selected from:
  Q61K (results in an amino acid substitution at position 61 in KRAS, from a glutamine (Q) to a lysine (K));
  Q61L (results in an amino acid substitution at position 61 in KRAS, from a glutamine (Q) to a leucine (L));

Q61R (results in an amino acid substitution at position 61 in KRAS, from a glutamine (Q) to an arginine (R)); and/or Q61H (results in an amino acid substitution at position 61 in KRAS, from a glutamine (Q) to a histidine (H)).

I.e. the cancer has cancer cells which harbor at least one KRAS gene mutation, wherein the KRAS gene mutation is selected from a mutation in the KRAS protein encoding gene at codons 12, 13 and/or 61 and is selected from G12C, G12R, G12S, G12A, G12D, G12V, G13C, G13R, G13S, G13A, G13D, Q61K, Q61L, Q61R and/or Q61H.

In particular, the cancer has cancer cells which harbor at least one KRAS gene mutation at codon 12 in exon 2, more preferably one or more of G12C, G12A, G12D, G12S and/or G12V. Further preferred, the cancer has cancer cells with at least one KRAS gene mutation selected from one or more of G12C and/or G12S.

The expression "the cancer has cancer cells which harbor/ have a RAS mutation" means that the cancer comprises such cancer cells, in particular it has a significant amount of such cancer cells. Whether cancer cells have a RAS gene mutation such as a KRAS gene mutation can be detected with methods known to the skilled person such as DNA sequencing or commercially available test systems, DNA-DNA hybridization and the like.

The RAS-positive disease can be a RAS-positive such as KRAS-positive adenocarcinoma.

The disease is most preferably selected from a RAS-positive, in particular KRAS-positive lung cancer or RAS-positive, in particular KRAS-positive pancreatic cancer. More preferably, the disease is a RAS-positive, in particular KRAS-positive NSCLC, in particular it is a RAS-positive, in particular KRAS-positive NSCLC adenocarcinoma.

The subject can be an animal or a human, in particular a mammal. Most preferably, the subject is a human.

Said compound of Formula (I) is a "PDEδ inhibitor" which means that it is able to interact with the phosphodiesterase delta subunit (PDEδ) hydrophobic pocket, namely the prenyl-binding pocket. The resulting inhibition of PDEδ is accompanied with deviated localization of RAS proteins and suppressed RAS growth signaling pathway which affects tumor growth. The PDEδ inhibitor in particular has one or more and most preferably all of the following effects in the RAS-positive like KRAS-positive cancer cells compared to untreated cancer cells of the same cell and tissue type:
  it inhibits cell viability;
  it induces apoptosis via the AMPK (AMP activated protein kinase)-mTOR (mammalian target of rapamycin) pathway;
  it inhibits colony formation;
  it increases the expression of proapoptotic protein Bax;
  it reduces the expression of anti-apoptotic protein Bcl-2; and/or
  it induces cleavage of Poly (ADP-ribose) polymerase (PARP).

This can be confirmed by means of an MTT assay, a colony formation assay and Western blotting, respectively.

Also contemplated by the present invention is any pharmaceutically acceptable salt, solvate, anhydrate as well as enantiomer and mixtures of enantiomers such as racemate of the PDEδ inhibitor of Formula (I).

As used herein, the term "solvate" refers to a complex of variable stoichiometry formed by a solute, i.e. the PDEδ inhibitor of Formula (I), and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical composition. The terms enantiomers and racemate are known to the skilled person.

The PDEδ inhibitor is in particular of Formula (Ia), i.e. is the (S)-enantiomer of Formula (I) which is also known as deltarasin:

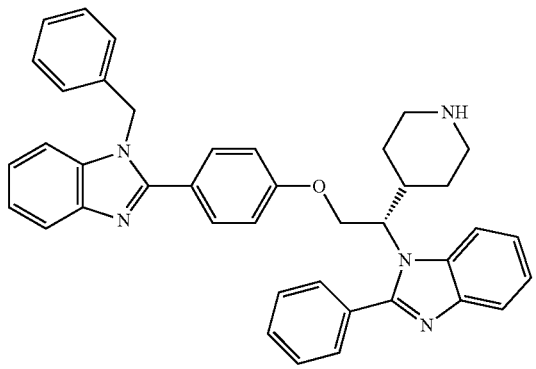

Formula (Ia)

A "direct autophagy inhibitor" is a compound which is able to directly inhibit autophagy in a subject. The expression "direct autophagy inhibitor" in particular means that it specifically targets autophagy regulators such as phosphoinositide 3-kinase (PI3K), in particular class III PI3K or Beclin-1 and/or specifically affects lysosomal processes such as the fusion of autophagosomes with lysosomes and/or their degradation. Autophagy regulators are the proteins such as kinases encoded by respective genes contributing either to the initiation of autophagy or to the inhibition of autophagy, namely they either activate or inhibit autophagy. In particular, a direct autophagy inhibitor is a compound specifically targeting autophagy regulators. "Targeting" autophagy regulators as used herein means that it either inhibits or enhances the activity of an autophagy regulator protein or increases or decreases the expression of an autophagy regulator encoded by a gene. A direct autophagy inhibitor is, thus, a compound that disrupts the autophagy pathway. Non-limiting examples of direct autophagy inhibitors include 3-Methyladenine (3-MA) or siRNA that results in a decrease in the expression of, for example, Autophagy-related protein 7, Autophagy protein 5 or LC3.

Compounds acting via scavenged radicals, in particular compounds acting via scavenged reactive oxygen species which indirectly affect autophagy via scavenged ROS like N-acetyl cysteine (NAC) are no direct autophagy inhibitors according to this invention. A direct autophagy inhibitor according to the present invention is in particular a compound which does not simultaneously suppress reactive oxygen species (ROS).

The direct autophagy inhibitor is preferably a phosphoinositide 3-kinase (PI3K) inhibitor, in particular a PI3K inhibitor which suppresses autophagy by inhibiting class III PI3K such as 3-methyladenine (3-MA) or wortmannin or the like. Class III PI3K is an autophagy regulator essential for the initiation of autophagy.

The direct autophagy inhibitor is most preferably 3-MA having a structure of Formula (II):

In particular embodiments of the method of the present invention, the PDEδ inhibitor is deltarasin having a structure of Formula (Ia):

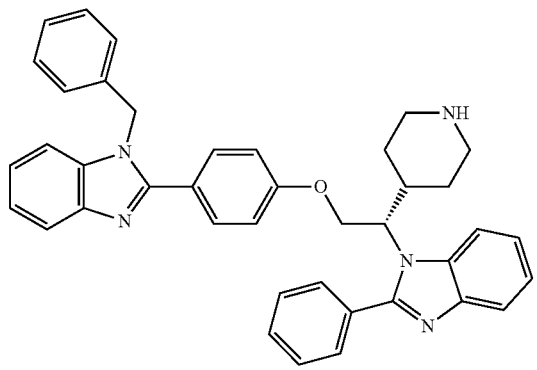

Formula (Ia)

and the direct autophagy inhibitor is 3-methyladenine having a structure of Formula (II):

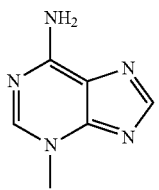

Formula (II)

"Treating" the RAS-positive disease preferably means one or more of inhibiting, reducing or preventing the proliferation of the cells, in particular cancer cells, and/or inducing apoptosis of cells, in particular cancer cells, i.e. inducing cell death. Treating a RAS-positive cancer in particular means inducing apoptosis of the cancer cells, i.e. cell death. Induction of apoptosis of cancer cells means a significant increase in the apoptosis, namely a significant increase in the percentage of apoptotic cells compared to untreated cancer cells of the same cell and tissue type. In particular, the percentage of apoptotic cells is increased by at least 5 percentage points, further preferred by at least 10 percentage points, more particular at least 18 percentage points, further preferred at least 15 percentage points compared to untreated cancer cells of the same cell and tissue type.

The expression "effective amount" as used herein generally denotes an amount sufficient to produce therapeutically desirable results, i.e. it means a therapeutically effective amount. The exact nature of the result may vary depending on the specific disorder which is treated. When the disorder is cancer, the result is usually an inhibition or reduction of the cancer growth or the amelioration of symptoms related to the cancer. According to the present invention it is preferably a reduction of the cancer growth in particular by an induction of apoptosis of the cancer cells.

In particular, the RAS-positive disease is KRAS-positive cancer such as KRAS-positive NSCLC and the administration of the PDEδ inhibitor and of the direct autophagy inhibitor induces apoptosis of the cancer cells of said cancer.

The effective amount of the PDEδ inhibitor and of the direct autophagy inhibitor may depend on the species, body weight, age and individual conditions of the subject and can be determined by standard procedures such as with cell cultures or experimental animals. A concentration of the PDEδ inhibitor such as of Formula (Ia) may, for example, be at least 2.5 µM such as about 5 µM. A concentration of the direct autophagy inhibitor can be, for example, at least 2.5 mM such as about 5 mM.

The direct autophagy inhibitor may be administered simultaneously, i.e. at the same time, with the PDEδ inhibitor or at any time interval before or after the administration of the PDEδ inhibitor. I.e. the PDEδ inhibitor and the direct autophagy inhibitor may be administered at the same time (simultaneously) or with certain time interval in between their administration, in particular they are administered simultaneously.

The PDEδ inhibitor and the direct autophagy inhibitor may be administered in form of either separate compositions such as pharmaceutical compositions or in form of one single composition such as one single pharmaceutical composition. A composition such as a pharmaceutical composition comprises the PDEδ inhibitor and/or the direct autophagy inhibitor and at least excipient such as a pharmaceutically tolerable excipient, in particular one or more of water, a buffer, a carrier, a salt, a diluent, a filler, a binder, a disintegrant, a lubricant, a coloring agent, a surfactant and a preservative. The composition such as the pharmaceutical composition can be present in solid, semisolid or liquid form. The composition according to the invention may be administered by an oral or parenteral route to the subject.

The composition such as the pharmaceutical composition may comprise further therapeutically effective ingredients such as compounds used for treating RAS-positive diseases, in particular for treating KRAS-positive cancer like KRAS-positive NSCLC.

A "pharmaceutical composition" is a finished dosage formulation in the form in which it can be used by the subject or administered to the subject, which contains the PDEδ inhibitor and/or the direct autophagy inhibitor and one or more pharmaceutically tolerable excipients, i.e. excipients which are well tolerated by the subject and do not negatively influence the therapeutic effect of the PDEδ inhibitor and the direct autophagy inhibitor. The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

The method of the present invention may further include steps carried out before administering the PDEδ inhibitor and of the direct autophagy inhibitor to the subject comprising:

obtaining a sample such as cancer cells from the subject;
testing said sample for one or more of the RAS activity such as KRAS activity, the RAS expression level such as the KRAS expression level and/or a RAS gene

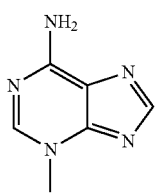

Formula (II)

mutation, in particular a KRAS gene mutation such as selected from G12C, G12R, G12S, G12A, G12D, G12V, G13C, G13R, G13S, G13A, G13D, Q61K, Q61L, Q61R and/or Q61H;

optionally correlating the level of RAS expression and/or RAS activity, in particular KRAS expression and/or KRAS activity, with outcome and if conditions are met, administrating the PDEδ inhibitor and of the direct autophagy inhibitor to said subject.

Further provided with the present invention is a method of potentiating the apoptotic activity of a PDEδ inhibitor in RAS-positive cells comprising contacting the cells with:

(i) the PDEδ inhibitor having a structure of Formula (I),

Formula (I)

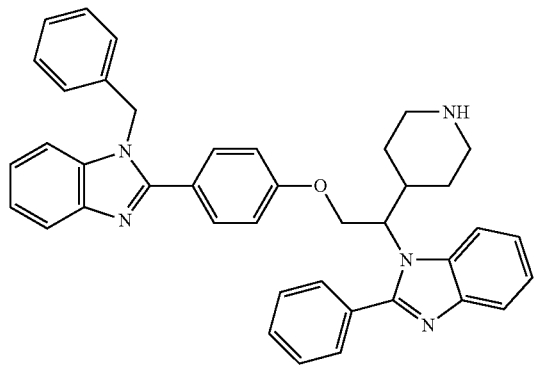

and (ii) a direct autophagy inhibitor.

The direct autophagy inhibitor of the present invention is effective for potentiating the apoptotic activity of the PDEδ inhibitor, i.e. for increasing the effectiveness of the PDEδ inhibitor to induce apoptosis of the cells, i.e. cell death. "Potentiating the apoptotic activity" as used herein means any measurable increase in the apoptosis when contacting the cells with the PDEδ inhibitor and the direct autophagy inhibitor compared to the use of the PDEδ inhibitor without the direct autophagy inhibitor such as an increase in the percentage of apoptotic cells of at least 5 percentage points, preferably at least 7 and in particular at least 8 percentage points when contacting the cells with the PDEδ inhibitor and the direct autophagy inhibitor compared to cells of the same cell and tissue type contacted with the PDEδ inhibitor without the direct autophagy inhibitor, wherein the PDEδ inhibitor is used in the same concentration as used when contacting the cells with the PDEδ inhibitor in combination with the direct autophagy inhibitor. I.e. the direct autophagy inhibitor in particular markedly enhances the PDEδ inhibitor-induced apoptosis. The percentage of total cell deaths and cell viability can be measured with the MTT assay.

The direct autophagy inhibitor preferably further promotes the cleavage of PARP present under the PDEδ inhibitor which can be determined with Western blotting and/or enhances the ROS production under the PDEδ inhibitor, i.e. leads to increased reactive oxygen species which can be determined with 2',7'-dichlorfluorescein-diacetate (DCF-DA) fluorescence staining. For example, the level of cleaved PARP is increased at least 10% and further preferred at least 20% and in particular at least 30% when contacting the cells with the direct autophagy inhibitor and the PDEδ inhibitor compared to cells contacted with the same concentration of PDEδ inhibitor but without the direct autophagy inhibitor.

The percentage of cells with ROS is preferably increased by at least 10 percentage points, preferably by at least 15 percentage points when contacting the cells with the direct autophagy inhibitor and the PDEδ inhibitor compared to cells contacted with the same concentration of the PDEδ inhibitor but without the direct autophagy inhibitor.

In particular embodiments of the present invention, the direct autophagy inhibitor increases the percentage of apoptotic cells and the cleavage of PARP and/or the ROS production as present under the PDEδ inhibitor, i.e. as present when the cells are contacted with the same concentration of the PDEδ inhibitor without the direct autophagy inhibitor.

In particular, the direct autophagy inhibitor inhibits autophagy induced by the PDEδ inhibitor which can be confirmed, for example, by means of a reduction of GFP-LC3 puncta formation determined with a respective assay using green fluorescent protein or a reduction in the level of LC3-II determined with Western blotting. In particular, the percentage of cells with GFP-LC3 puncta formation under the PDEδ inhibitor when used without the direct autophagy inhibitor is decreased by at least 10 percentage points, more preferably by at least 20 percentage points when applying the same concentration of the PDEδ inhibitor in combination with the direct autophagy inhibitor.

The step of contacting the cells with the PDEδ inhibitor and the direct autophagy inhibitor may be carried out by applying at least one incubation solution comprising the PDEδ inhibitor and/or the direct autophagy inhibitor to said cells which incubation solution may further comprise suitable excipients such as solvents, buffers or a suitable growth medium. Alternatively, contacting the cells with the PDEδ inhibitor and the direct autophagy inhibitor may be carried out by administering the PDEδ inhibitor and the direct autophagy inhibitor to a subject comprising said RAS-positive cells, in particular to a subject suffering from RAS-positive cancer such as KRAS-positive cancer like KRAS-positive NSCLC. The PDEδ inhibitor and the direct autophagy inhibitor may be administered by an oral or parenteral route to a subject, preferably a mammal like a human. The PDEδ inhibitor and the direct autophagy inhibitor may be administered in form of separate compositions like pharmaceutical compositions or alternatively one single composition, in particular one single pharmaceutical composition, comprising the PDEδ inhibitor and/or the direct autophagy inhibitor and at least one excipient such as one or more of water, a salt, a buffer, a carrier, a diluent, a filler, a binder, a disintegrant, a lubricant, a coloring agent, a surfactant and a preservative. The composition can be present in solid, semisolid or liquid form.

The RAS-positive cells can be from a tissue sample or another cell-containing sample from a subject, in particular a mammal such as a human.

Preferably, the RAS-positive cells are KRAS-positive cells, i.e. they have an enhanced expression or enhanced activity of a KRAS protein, in particular a KRAS mutant protein is expressed. The cells preferably have at least one KRAS gene mutation, wherein the KRAS gene mutation is selected from a mutation in the KRAS protein encoding gene at codons 12, 13 and/or 61 and is selected from G12C, G12R, G12S, G12A, G12D, G12V, G13C, G13R, G13S, G13A, G13D, Q61K, Q61L, Q61R and/or Q61H, in particular at least one or more of G12C and/or G12S In particular, the RAS-positive, in particular KRAS-positive cells are cancer cells, i.e. from a cancer such as a pancreatic cancer or a lung cancer. The cancer is in particular an adenocarcinoma. More preferably, the RAS-positive cells are KRAS-positive cells from a NSCLC, in particular a NSCLC adenocarcinoma, and have at least one KRAS gene mutation at codon 12 in exon 2, more preferably one or more of G12C, G12A, G12D, G12S and/or G12V. Further preferred, the cells have at least one KRAS gene mutation selected from one or more of G12C and/or G12S.

In particular embodiments of the method of the present invention, the PDEδ inhibitor is deltarasin having a structure of Formula (Ia):

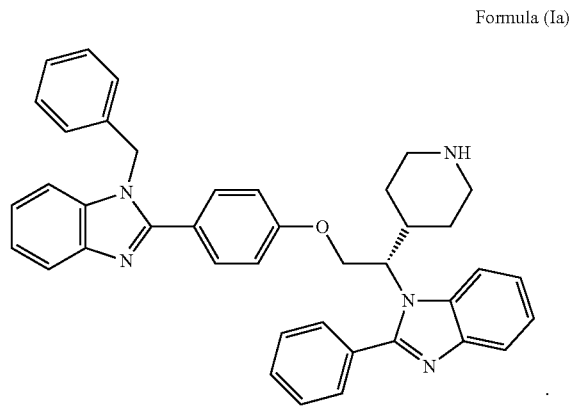 [SMILES: c1ccc(Cn2c(-c3ccc(OC[C@H](C4CCNCC4)n4c(-c5ccccc5)nc5ccccc54)cc3)nc3ccccc32)cc1]

Formula (Ia)

and the direct autophagy inhibitor is 3-methyladenine having a structure of Formula (II):

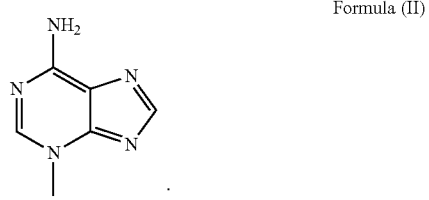

Formula (II)

The cells may be contacted with the PDEδ inhibitor and the direct autophagy inhibitor simultaneously, i.e. at the same time, or alternatively the cell can be contacted with the direct autophagy inhibitor at any time interval before or after the administration of the PDEδ inhibitor. The cells are preferably contacted with the PDEδ inhibitor and the direct autophagy inhibitor at the same time, i.e. simultaneously. Alternatively, the direct autophagy inhibitor is applied at least 30 min before the PDEδ inhibitor.

The cells are preferably contacted with the PDEδ inhibitor and the direct autophagy inhibitor for at least 12 h, in particular for at least 24 h such as for about 24 h, 48 h or 72 h.

The concentration of the PDEδ inhibitor for contacting the cells is preferably at least 2.5 µM, more preferably at least about 5 µM such as about 5 µM. The concentration of the direct autophagy inhibitor for contacting the cells is preferably at least 2.5 mM, in particular at least about 5 mM such as about 5 mM.

In embodiments of the present invention, the cancer cells are contacted with a concentration of at least 2.5 µM of the PDEδ inhibitor and at least 2.5 mM of the direct autophagy inhibitor for at least 12 h.

In particular embodiments of the present invention, the cancer cells are contacted with a concentration of about 5 µM of the PDEδ inhibitor and about 5 mM of the direct autophagy inhibitor for at least 24 h, wherein the PDEδ inhibitor is deltarasin having a structure of Formula (Ia) and wherein the direct autophagy inhibitor is 3-methyladenine having a structure of Formula (II).

In a further aspect, the present invention provides a method of treating a subject suffering from a RAS-positive lung cancer comprising administering an effective amount of a composition such as a pharmaceutical composition comprising a PDEδ inhibitor having a structure of Formula (I):

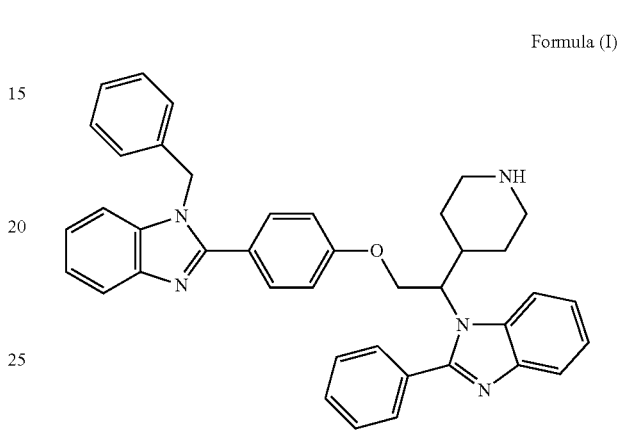

Formula (I)

to the subject.

The administration of the effective dose of the composition such as pharmaceutical composition comprising the PDEδ inhibitor in particular induces apoptosis in the cancer cells by inhibiting the interaction of KRAS with PDEδ.

In particular:
the phosphorylation of downstream signaling effectors c-Raf, Akt and ERK is inhibited by the administration of the PDEδ inhibitor compared to untreated subjects and cells, respectively, which can be confirmed with Western Blotting; and/or the phosphorylation of mTOR and Ribosomal protein S6 kinase beta-1 (p70S6K) is inhibited by the administration of the PDEδ inhibitor compared to untreated subjects and cells, respectively, indicating activation of the AMPK-mTOR dependent autophagy inducing pathway which can be confirmed by means of Western Blotting.

The composition such as the pharmaceutical composition comprises the PDEδ inhibitor and at least one excipient, in particular a pharmaceutically tolerable excipient such as a carrier, a salt, a buffer, water, a diluent, a filler, a binder, a disintegrant, a lubricant, a coloring agent, a surfactant and a preservative or a combination thereof.

The composition such as the pharmaceutical composition in particular further comprises a direct autophagy inhibitor. Said direct autophagy inhibitor in particular inhibits the autophagy induced by the PDEδ inhibitor and potentiates the apoptotic activity of the PDEδ inhibitor such as involving an increased production of reactive oxygen species and/or an increased PARP cleavage.

The direct autophagy inhibitor is preferably an inhibitor of class III phosphoinositide 3-kinase and most preferably it is 3-methyladenine having a structure of Formula (II):

Formula (II)

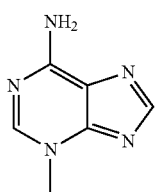

The PDEδ inhibitor is more preferably deltarasin having a structure of Formula (Ia):

Formula (Ia)

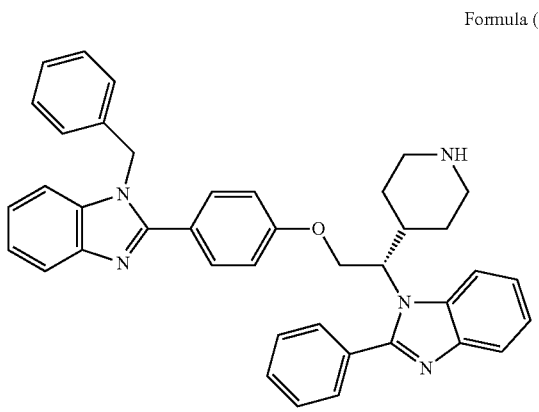

and the pharmaceutical composition further comprises a direct autophagy inhibitor, which is 3-methyladenine having a structure of Formula (II).

The RAS-positive lung cancer is preferably a KRAS-positive lung cancer, more preferably a KRAS-positive NSCLC and in particular a KRAS-positive NSCLC adenocarcinoma.

In particular, the KRAS-positive lung cancer has cancer cells having at least one KRAS gene mutation at codon 12 in exon 2, more preferably one or more of G12C, G12A, G12D, G12S and/or G12V. Further preferred, the cancer cells have at least one KRAS gene mutation selected from one or more of G12C and/or G12S.

In another aspect, the present invention refers to a kit comprising an effective dose of:

(i) a PDEδ inhibitor having a structure of Formula (I),

Formula (I)

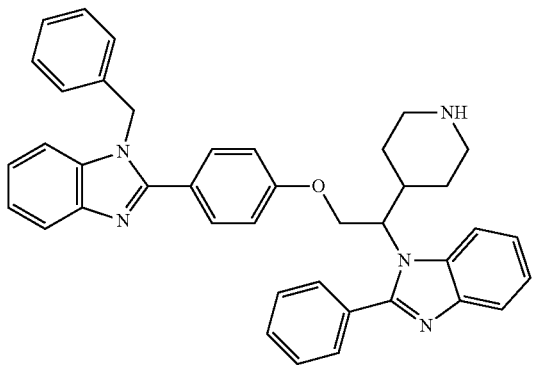

and (ii) a direct autophagy inhibitor.

The PDEδ inhibitor is preferably deltarasin having a structure of Formula (Ia):

Formula (Ia)

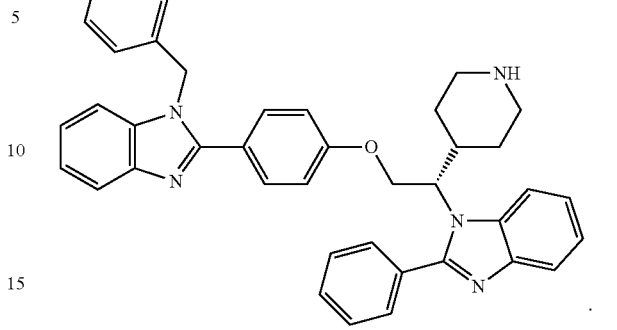

and the direct autophagy inhibitor is preferably 3-methyladenine having a structure of Formula (II):

Formula (II)

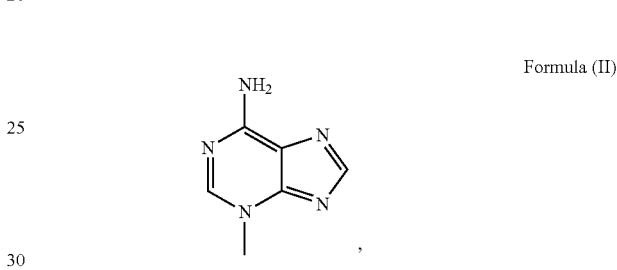

The kit may further comprise an instruction leaflet and/or excipients, in particular pharmaceutically acceptable excipients, such as a carrier, a salt, a buffer, water, a diluent, a filler, a binder, a disintegrant, a lubricant, a coloring agent, a surfactant and a preservative or a combination thereof. The skilled person is able to select suitable excipients. Still further, the kit may comprise at least one container.

The PDEδ inhibitor and the direct autophagy inhibitor according to the invention can be present in solid, semisolid or liquid form to be administered by an oral or parenteral route to a subject, preferably a human.

Further provided by the present invention is a pharmaceutical composition comprising:

(i) a PDEδ inhibitor having a structure of Formula (I), in particular of Formula (Ia), and (ii) a direct autophagy inhibitor, in particular of Formula (II), and (iii) at least one pharmaceutically acceptable excipient, such as selected from one or more of a carrier, a salt, a buffer, water, a diluent, a filler, a binder, a disintegrant, a lubricant, a coloring agent, a surfactant and a preservative or a combination thereof.

According to the invention is also a PDEδ inhibitor of Formula (I), in particular of Formula (Ia), for use as a medicament for the treatment of KRAS-positive NSCLC, wherein the PDEδ inhibitor is used in combination with a direct autophagy inhibitor, in particular of Formula (II). Another aspect of the present invention refers to the use of the PDEδ inhibitor of Formula (I), in particular of Formula (Ia), for preparing a medicament for use for the treatment of KRAS-positive NSCLC, wherein the PDEδ inhibitor is used in combination with a direct autophagy inhibitor, in particular of Formula (II). The present invention also relates to the use of a combination of a PDEδ inhibitor of Formula (I), in particular of Formula (Ia), and a direct autophagy inhibitor, in particular of Formula (II), for inducing apoptosis, in particular for increasing the percentage of apoptotic cells, the cleavage of PARP and the production of reactive oxygen species.

EXAMPLES

Materials and Methods

Cell Lines and Cell Cultures

A549, H358 and PANC-1 cancer cells were obtained from the American Type Culture Collection and maintained in an environment of 5% $CO_2$ at 37° C. in RPMI-1640 medium supplemented with 10% fetal bovine serum (FBS) 2 mM L-glutamine, 100 units/mL penicillin and 100 µg/mL streptomycin.

Chemical Reagents and Antibodies

Deltarasin and 3-MA were purchased from Selleck Chemicals Co. Ltd, Compound C was purchased from Sigma-Aldrich, and they were dissolved in dimethyl sulfoxide (DMSO) to a 10 mM or 50 mM stock concentration and stored as small aliquots at −20° C. until further use. GAPDH, c-Raf, p-c-Raf, p-Akt (Ser473), p-ERK (Thr202/Thy204), ERK, PARP, Bax, Bcl-2, p-p70s6k, p70s6k, p-AMPK, AMPK, LC3 antibodies were purchased from Cell Signaling Technology (p=phosphorylated). Anti-AKT, KRAS antibody was purchased from Santa Cruz Biotechnology.

Cell Viability Assay 3000 cells were seeded at 96-well plates and cultured overnight for cell adhesion, and treated with DMSO or various concentrations of deltarasin for 72 h. At the end of the incubation, 10 µl of MTT (5 mg/mL, Sigma) were added into each well for 4 h at 37° C., then the crystals were dissolved in 100 µl of the resolved solution (10% SDS and 0.1 mM HCL). The absorbance at 570 nm was measured using a microplate reader (Tecan, Morrisville, N.C., USA). The cell viability was calculated relative to untreated controls. At least 3 independent experiments were performed and the data were plotted as curve graph.

Cell Apoptosis Assays

Apoptosis was measured using the Annexin V-FITC apoptosis detection kit (BD Biosciences, San Jose, Calif., USA), according to the manufacturer protocol. Briefly, A549, H358 and PANC-1 cells ($1.0 \times 10^5$ cells/well) were allowed to attach in a six-well plate for 24 h, cells were treated with deltarasin for 24 h. Subsequently, cells were trypsinized, washed with PBS and stained with 100 µL binding buffer containing 2 µl Annexin-V FITC (2.5 µg/ml) and 5 µl propidium iodide (PI) (50 µg/ml) incubated in the dark at room temperature for 15 min, before further addition of 400 µl of 1×Annexin-binding buffer. The stained cells were analyzed quantitatively using a BD Aria III Flow Cytometer (BD Biosciences, San Jose, Calif., USA). Data were analyzed by Flow Jo software.

Colony Formation Assay

Detailed procedures of colony formation assay were described previously (Franken, N. A., et al., Nature protocols, 2006, 1(5):2315-2319). A549 cells were seeded in a six-well plate at a density of 500 cells per well. The cells were exposed to various concentrations of deltarasin. After 10-14 days, the colonies were fixed with 4% paraformaldehyde and stained with 0.5% (0.5% w/v) crystal violet solutions, the number of colonies were counted under a dissecting microscope.

Transient Transfection and Detection of Autophagy

GFP-LC3 expression vector was utilized to monitor and quantify the induction of autophagy following the $3^{rd}$ autophagy guidelines. A549 cells were seeded at a density of $2 \times 10^5$ cells/well in 6-well plates, according to the manufacturers instructions. Lipofectamine™ 2000 was incubated with GFP-LC3 in Opti-MEM reduced serum medium for 20 min at room temperature. The mixture was added drop by drop to the cells and then incubated for 4-6 h. The DNA/Lipofectamine™ 2000 medium was replaced by fresh medium and cultured for another 24 h. Then, 5 µM deltarasin or 5 mM 3-MA was added to the cells, after the end of the treatment period, autophagy was measured by counting the increased percentage of cells with punctate GFP-LC3 fluorescence using API Delta Vision Live-cell Imaging System (Applied Precision Inc., GE Healthcare Company, Washington, USA)(51). The percentage of autophagic cells was calculated by counting the number of the cells showing increased punctuate pattern of LC3 fluorescence (≥10 dots/cell) in immunofluorescence positive cells over the total number of cells in the same field. A minimum of 300 cells from randomly selected fields were scored.

Detection of ROS Production by DCF-DA

Intracellular ROS generation was measured by DCF-DA fluorescence probe using flow cytometry. Briefly, A549, H358 and PANC-1 cells ($1 \times 10^5$ cells/well) were seeded in a six-well plate, and different concentrations of deltarasin were added into the wells. After treatment with deltarasin for 24 h, the treated cells were detached with trypsin, and washed twice with PBS and incubated with 10 µM DCF-DA for 30 min at 37° C. in the dark, the fluorescence-stained cells were then analyzed using a FACS BD Aria III flow cytometer.

Immunofluorescence

Cells were plated on 6-well plates and grown overnight, then treated with 5 µM deltarasin or 5 mM 3-MA for 24 h. Cells were fixed with 4% paraformaldehyde for 20 min at 4° C., followed by permeabilized with 0.2% Triton X-100 in PBS for 10 min. Subsequently, the cells were blocked with 2% BSA/PBS for 30 min at room temperature, then incubated with KRAS antibody (1:100) overnight at 4° C., followed by the secondary antibody (1:500) for 1 h at room temperature. The nuclear was stained with 1 µg/ml Hoechst staining for 10 min in the dark. The cells were visualized using fluorescent microscopy.

RAS Activation Assay and Immunoblotting

A549 cells were treated with deltarasin for 24 h at 5 µM. Cells were lysed in lysis buffer, adjusted the volume of each sample to 1 ml with 1×Assay Lysis Buffer. Then 40 µl of the Raf1 RBD Agarose bead slurry was swiftly added to each samples. The samples were incubated at 4° C. for 1 h with gentle agitation. The beads were washed 3 times with cold lysis buffer, and bounded protein was resuspended in 40 µl of 2×reducing SDS-PAGE sample buffer and heated at 100° C. for 5 min. The level of total RAS was detected after SDS-PAGE followed by Western blot.

Western Blot Analysis

Cells were washed twice with cold PBS and then lysed in RIPA lysis buffer containing protease and phosphatase inhibitors. Protein concentration of the cell lysate was measured by using the Bio-Rad protein assay kit (Bio-Rad, Philadelphia, Pa., USA). After equalizing the protein concentrations of the samples, 5×laemmli buffer was added and boiled at 100° C. for 5 min. Equal amounts of protein (20-40 µg per lane) were separated with a 10% SDS-PAGE gel, then the separated proteins were transferred to a nitrocellulose (NC) membrane, which was then exposed to 5% non-fat dry milk in TBS contains 0.1% Tween 20 (0.1% TBST) for 1 h at room temperature with constant agitation, followed by overnight incubation at 4° C. with primary anti-bodies. After washing 3 times with TBST, the membranes were incubated with secondary rabbit or mouse fluorescent antibodies, then the signal intensity of the membranes was detected by anLI-COR Odessy scanner (Belfast, Me., USA). All primary antibodies were diluted in 1:1000, while their recommended secondary antibodies were diluted in 1:10000.

Statistical Analysis

Descriptive analytical data were presented as means±SEM. Statistical analysis was conducted using Graph Prim5.0. One-way analysis of variance (ANOVA) or student's t test was used to assess significant differences between datasets. Values of less than 0.05 were considered as significant.

Example 1

Apoptotic Activity of Deltarasin in Non-Small Cell Lung Cancer Cells

Figure 1B:
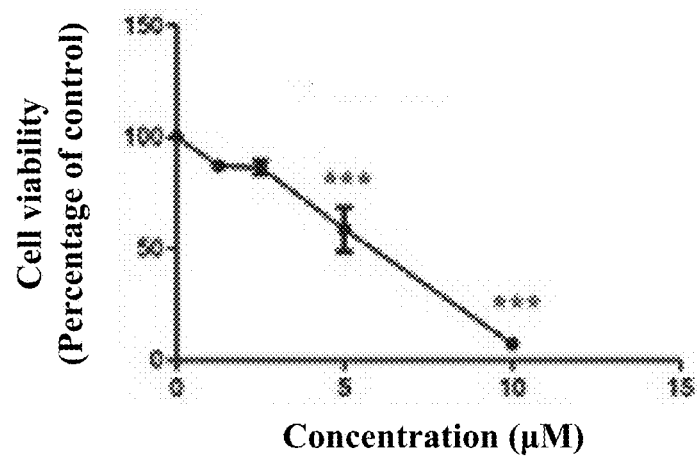
Figure 1C:
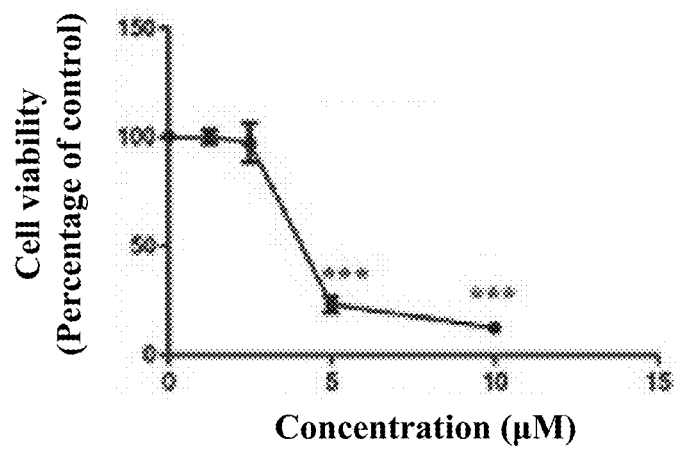

Zimmermann et. al. previously demonstrated the anticancer effect of deltarasin on pancreatic cancer cell lines, including PANC-1 with a KRAS G12D mutation. In this example, it has been examined if deltarasin can also induce cytotoxic effects on lung cancer cell lines, since lung cancers have an even higher frequency of KRAS mutations than pancreatic cancer in the clinic. A549 and H358 cell lines, which harbor KRAS G12S and G12C point mutations respectively, were used with PANC-1 cells used as a positive control. As shown in FIG. 1A to FIG. 1C, after treatment with deltarasin for 72 h, deltarasin significantly inhibited the cell viability in PANC-1 cells as well as in A549 and H358 cells in a dose dependent manner. The $IC_{50}$ values of the three cell lines were 3.86±0.96 µM, 5.29±0.7 µM, 4.21±0.72 µM respectively. The $IC_{50}$ value for PANC-1 cells is similar to that reported previously (Zimmermann, G. et al. Nature, 2013, 497(7451):638-642).

Figure 1D:
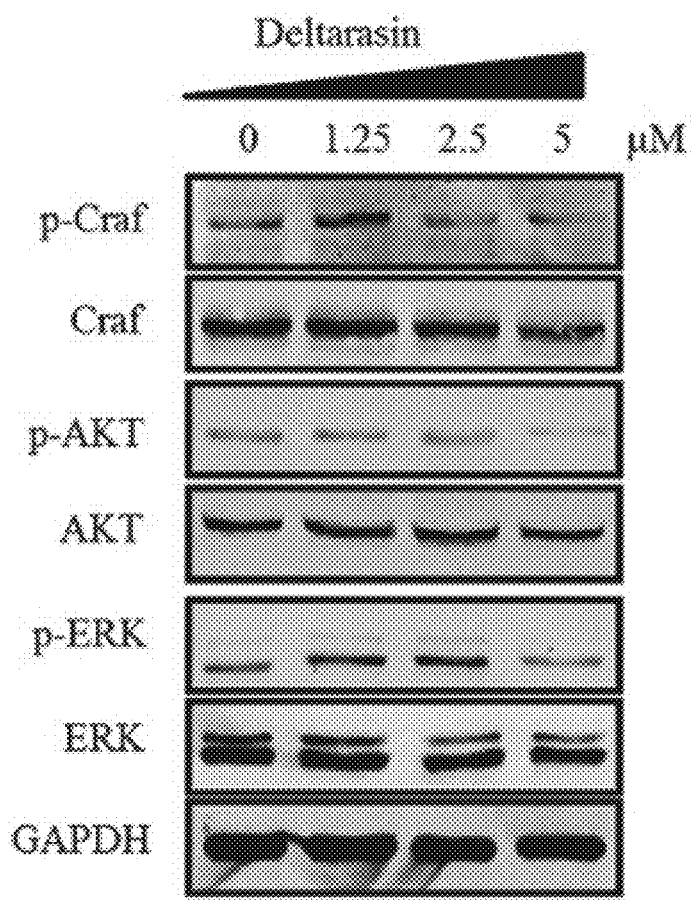
Figure 1E:
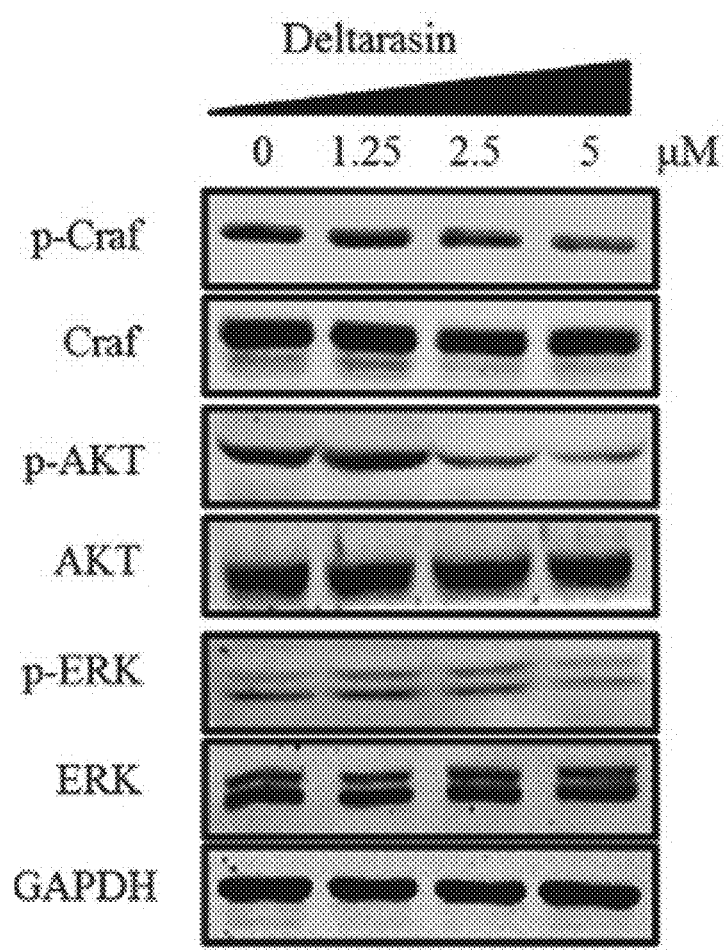
Figure 1F:
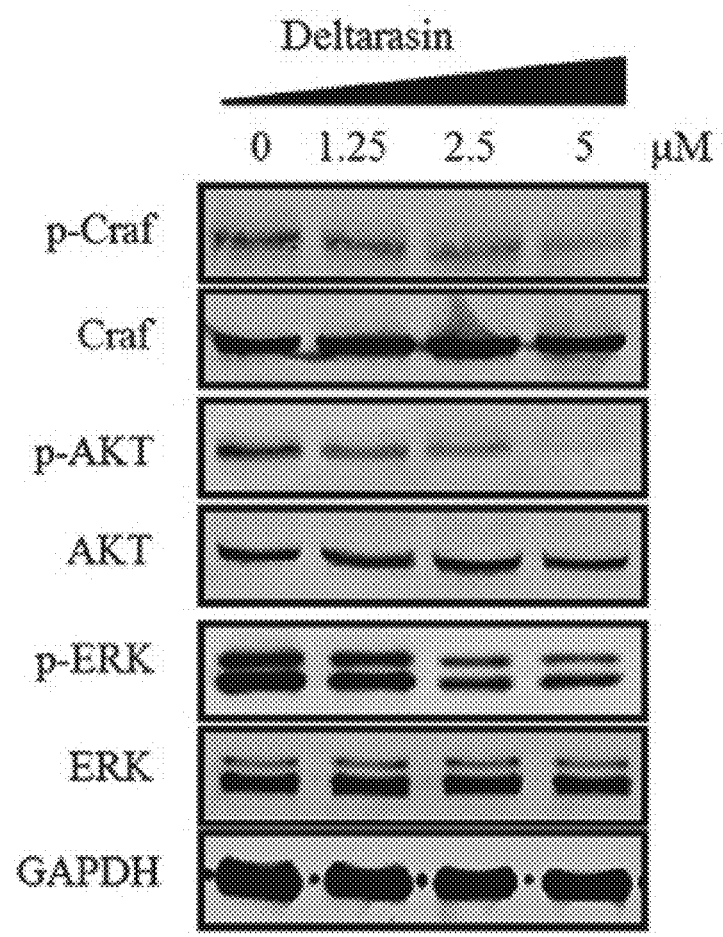

RAS, when in its active-GTP bound state, will translocate from the cytoplasm to the plasma membrane, then bind to its downstream effector kinase c-Raf, and subsequently turn on the two downstream growth and anti-apoptotic signaling pathways, the Raf/MEK/ERK and PI3K/Akt signaling cascades. Deltarasin is the first compound reported to block KRAS and PDEδ interaction and suppress Raf/MEK/ERK and PI3K/Akt signaling. It has been further examined whether deltarasin can suppress phosphorylation levels of c-Raf, Akt and ERK in PANC-1 pancreatic cancer cells as well as lung cancer cells. Western blot results showed that deltarasin inhibited c-Raf, Akt and ERK phosphorylation in all three cell lines after 24 h treatment (see FIG. 1D to 1F).

Example 2

Induction of Apoptosis in A549 KRAS-Positive NSCLC Cell Line by Deltarasin

Figure 2A:
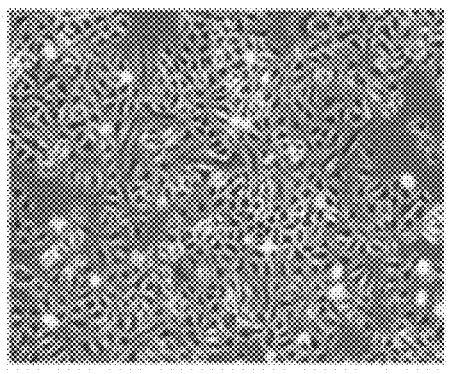
FIGS. 2A through 2H show the apoptotic activity of deltarasin in A549 cells.
Figure 2C:
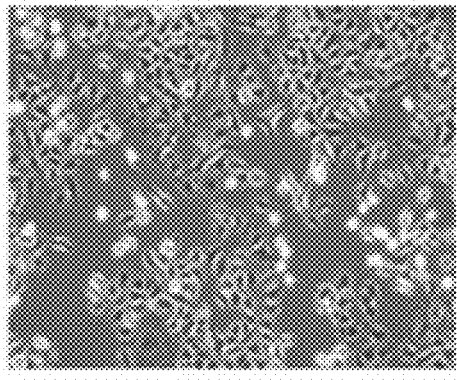
Figure 2B:
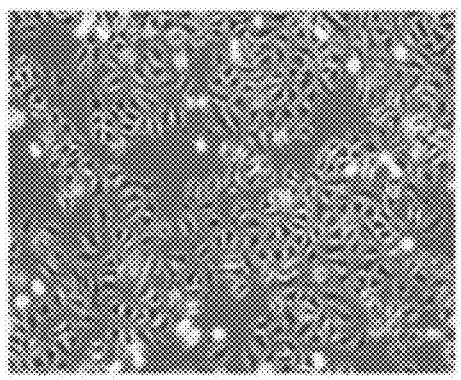
Figure 2D:
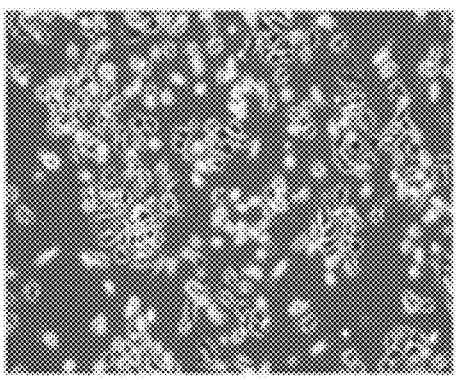
Figure 2E:
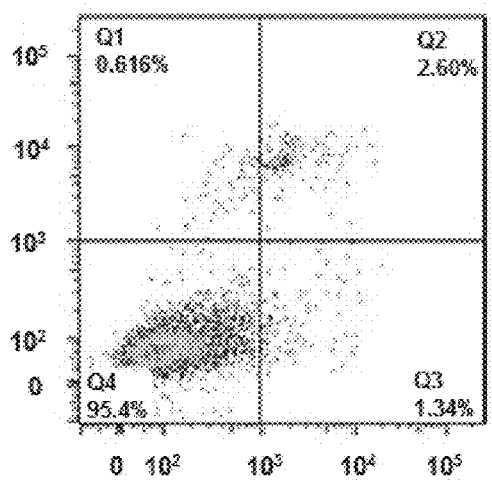
Figure 2F:
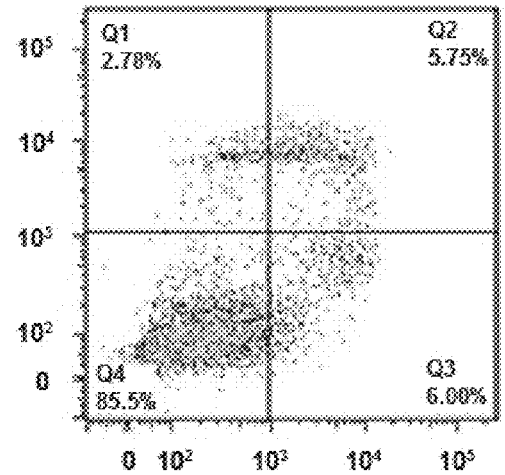
Figure 2G:
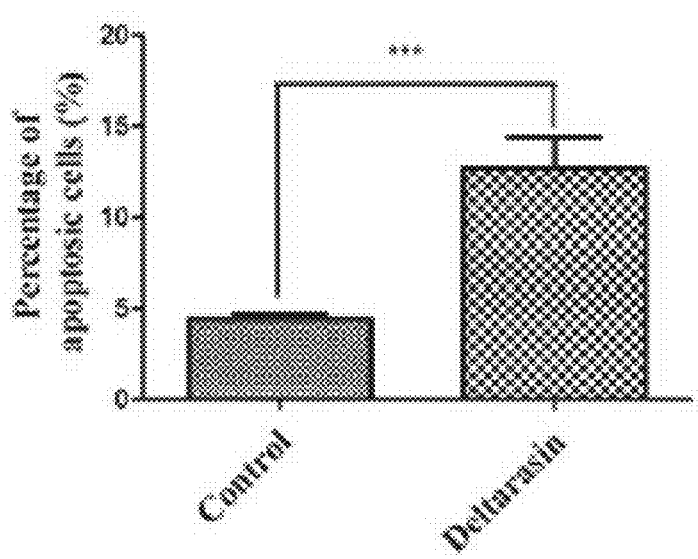
Figure 2H:
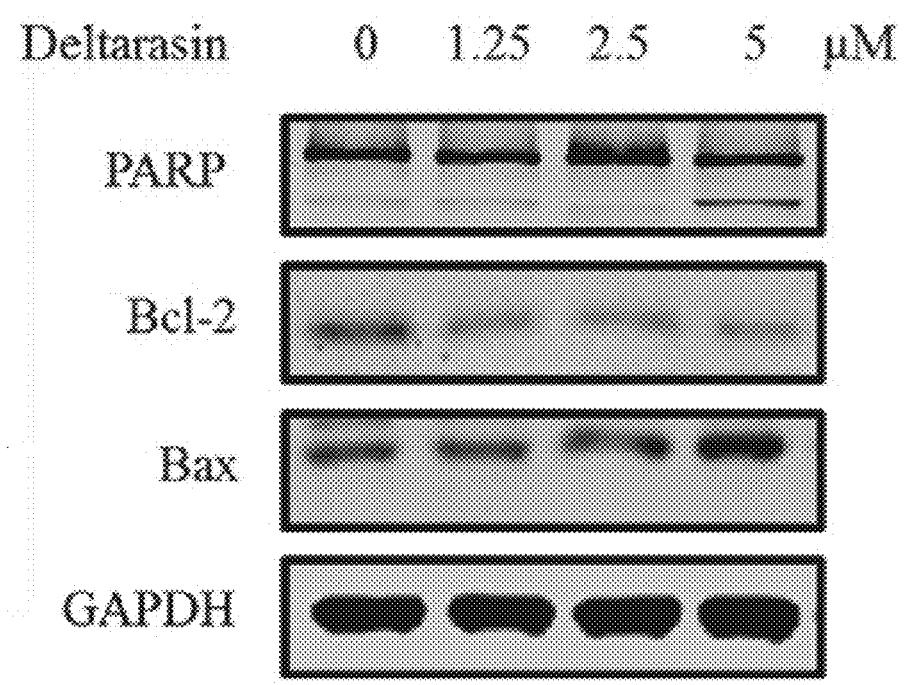

Using A549 cells as a representative lung cancer cell line with KRAS mutation, it has been determined whether the observed growth inhibition was due to apoptosis or necrosis. As illustrated in FIG. 2A to 2D, after treatment with deltarasin, a proportion of A549 cells detached from the culture dish. These cells showed cell shrinkage and rounding, which are typical apoptotic features. Next, by using Annexin V-FITC/PI staining followed by flow cytometry analysis, the percentage of apoptotic and necrotic cells were quantitatively measured. Results showed that deltarasin significantly induced apoptosis in A549 cells when compared with the untreated cells (FIG. 2E to 2G). Furthermore, to examine deltarasin-induced apoptosis in A549 cells, the expression levels of several pro- and anti-apoptotic proteins were analyzed by Western blotting. Results showed that an increase in the expression of pro-apoptotic protein Bax and a reduction of expression of anti-apoptotic protein Bcl-2 was observed in the deltarasin-treated cells. In addition, deltarasin treatment resulted in induction of the cleavage of PARP at 5 µM (FIG. 2H), also consistent with apoptosis. Taken together, these results prove that deltarasin can induce apoptosis in lung cancer cells in addition to pancreatic cancer cells.

Example 3

Figure 3A:
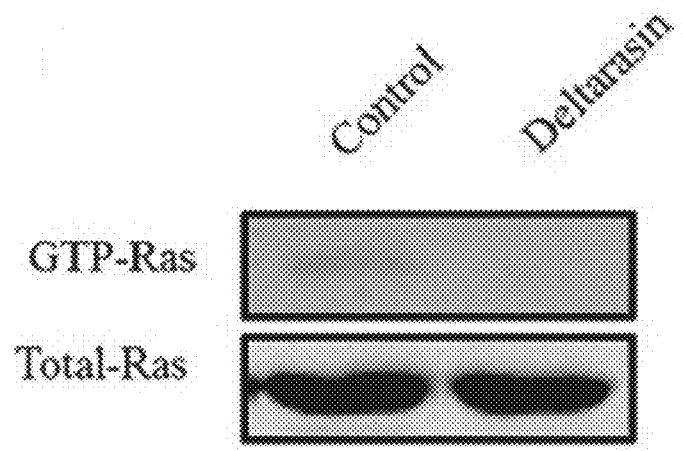
FIGS. 3A through 3I refer to the binding of GTP to RAS, the interaction of KRAS with PDEδ and the suppression of lung cancer cell growth.
Figure 3B:
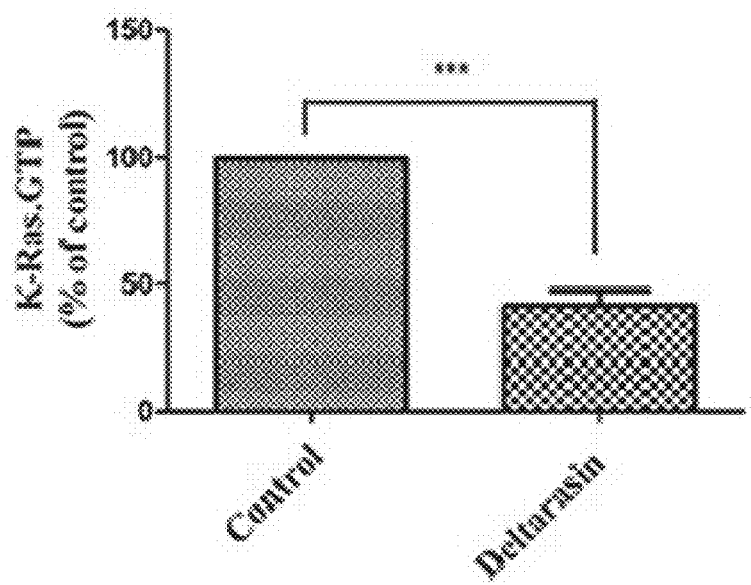
Figure 3C:
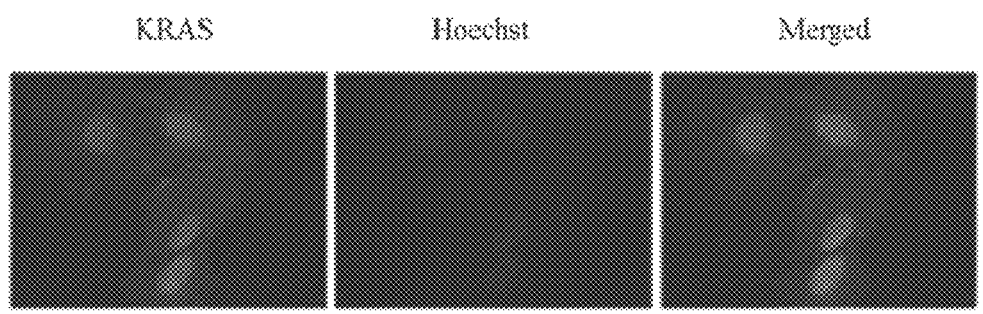
Figure 3D:
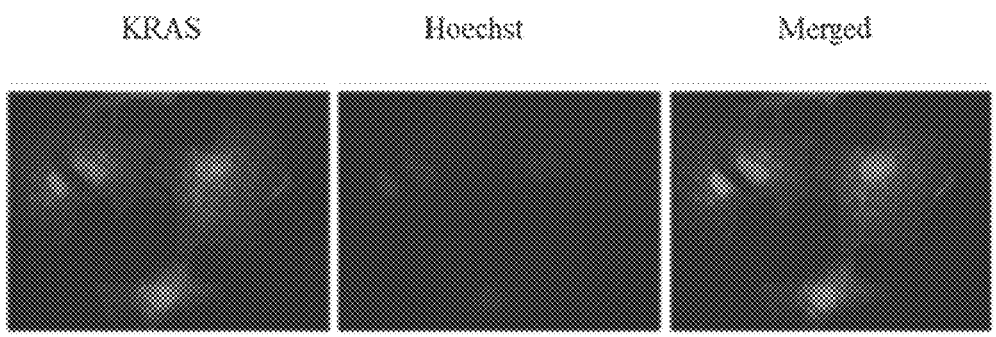
Figure 3E:
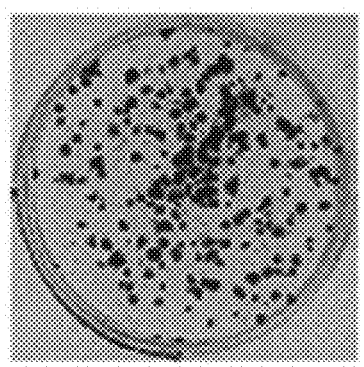
Figure 3G:
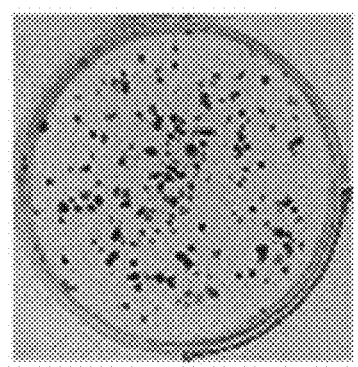
Figure 3F:
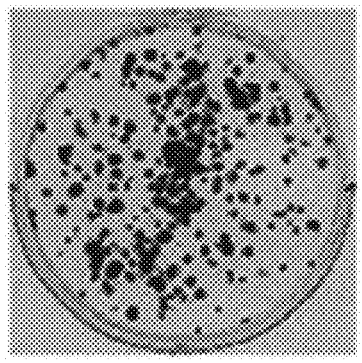
Figure 3H:
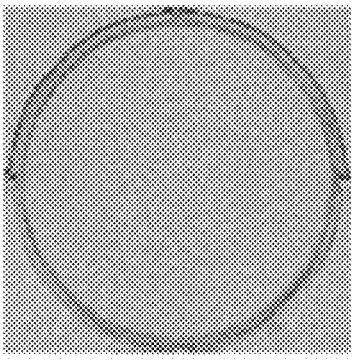
Figure 3I:
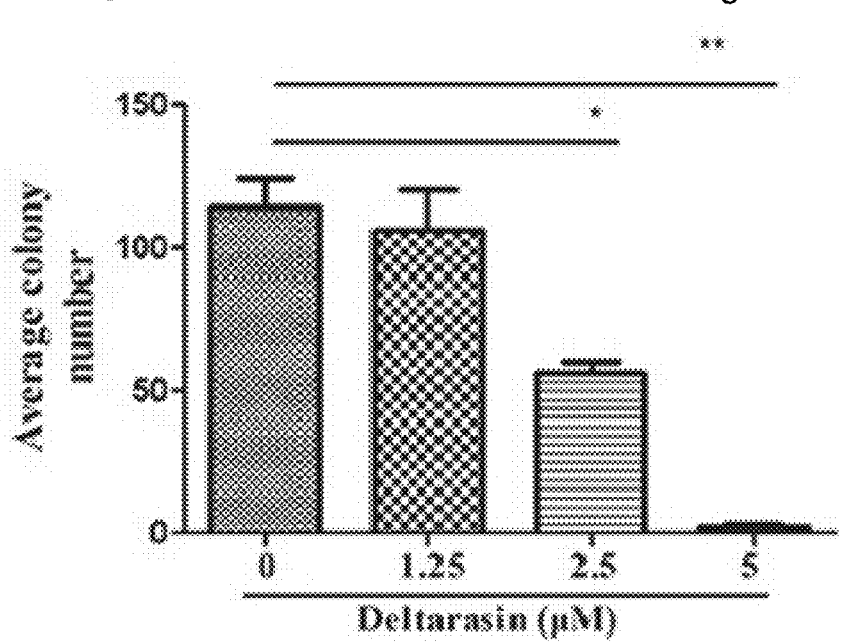

Inhibition of the Interaction of KRAS with PDEδ and its Downstream Signaling Pathway by Deltarasin As shown in FIGS. 3A and 3B, similar to the results previously reported in PANC1 pancreatic cancer cells, treatment of A549 cells with deltarasin significantly inhibited the binding of GTP to c-Raf-1 binding domain, suggesting that deltarasin is able to compete with the GTP binding pocket. Furthermore, deltarasin treatment reduced the amount of KRAS protein at the plasma membrane and displaced KRAS into the cytoplasm while in the control untreated cells, KRAS was mainly localized at the plasma membrane (FIGS. 3C and 3D). The above observations confirm that deltarasin can also inhibit the interaction of KRAS with PDEδ and suppresses the RAS downstream signaling pathways in NSCLC cells.

Subsequently, the effect of deltarasin on cell colony formation activity in A549 has been further examined as indicated in FIG. 3E to 3H, the results confirm that deltarasin significantly inhibits the colony formation capacity of A549 cells. Notably, when the concentration of deltarasin reached 5 µM, A549 cells formed no visible colonies after 10 days treatment. These data suggest that deltarasin not only suppresses GTP-RAS binding and KRAS membrane translocation but also strongly suppresses NSCLC cell growth.

Example 4

Induction of Autophagy in NSCLC Cells by Deltarasin

Figure 4A:
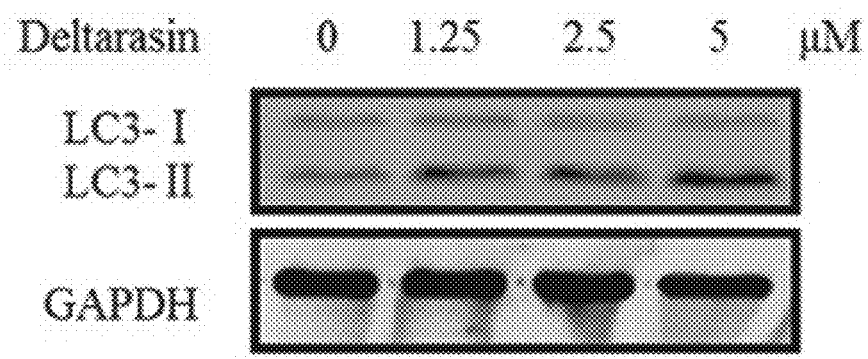
FIGS. 4A through 4K show that autophagy induced by deltarasin can be inhibited by the direct autophagy inhibitor 3-MA in pancreatic and NSCLC cells. The conversion of LC3-I to LC3-II was determined by Western blot with GAPDH as a loading control.
Figure 4B:
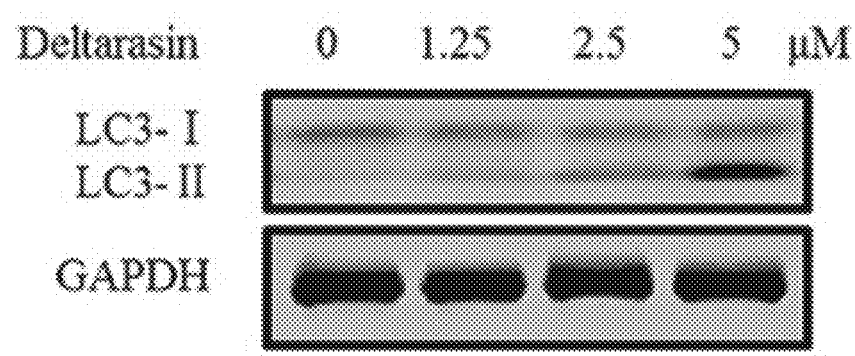
Figure 4C:
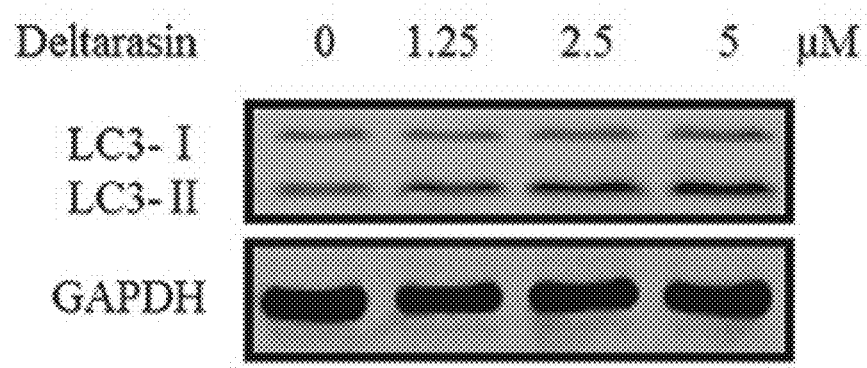
Figure 4D:
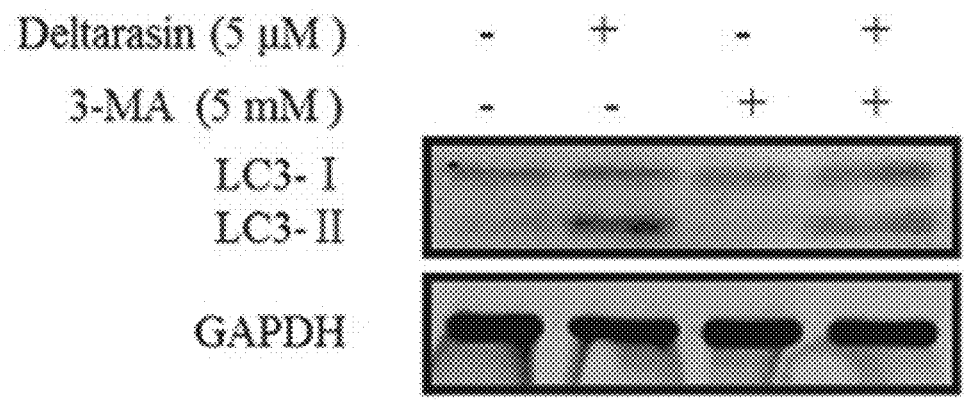
Figure 4E:
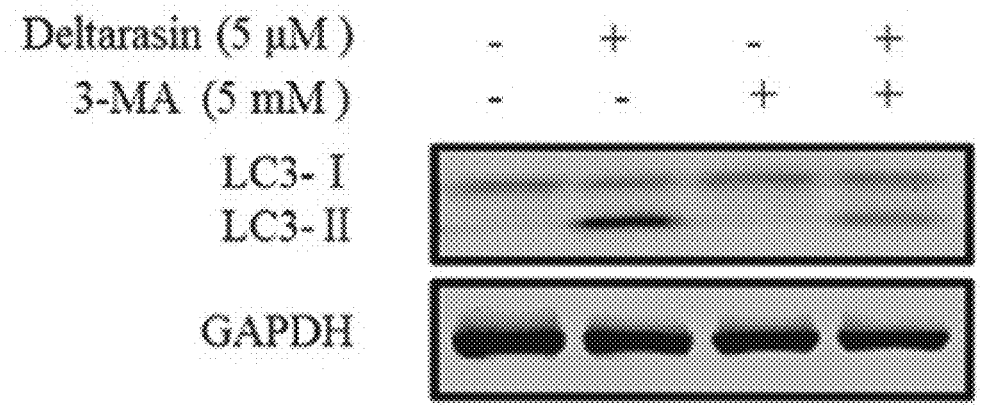
Figure 4F:
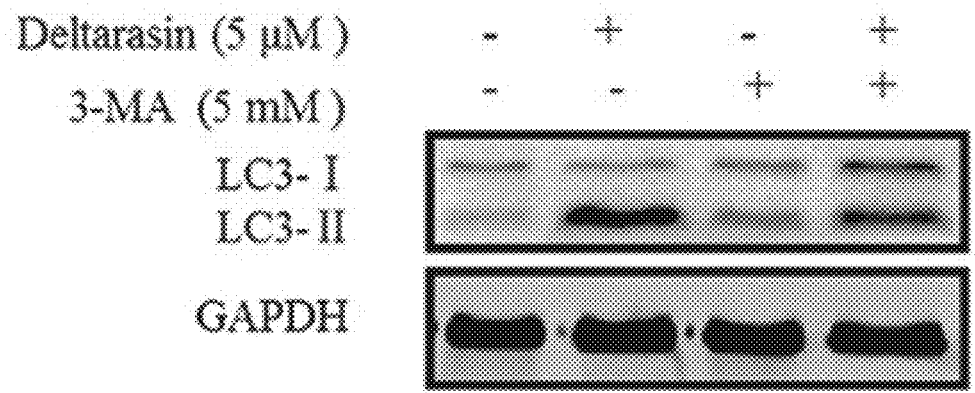
Figure 4G:
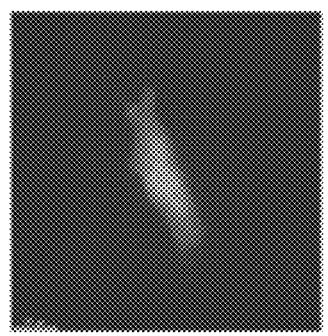
Figure 4I:
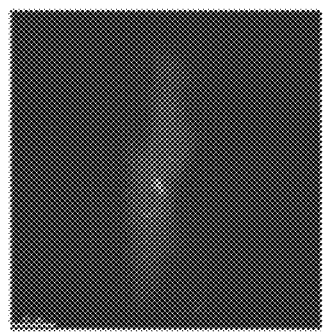
Figure 4H:
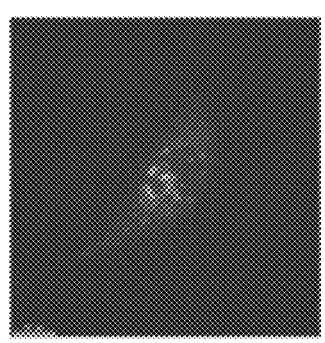
Figure 4J:
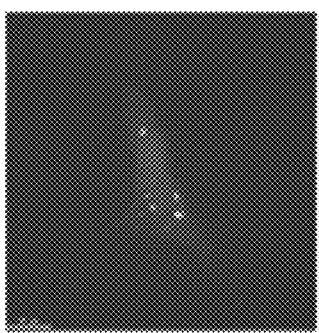
Figure 4K:
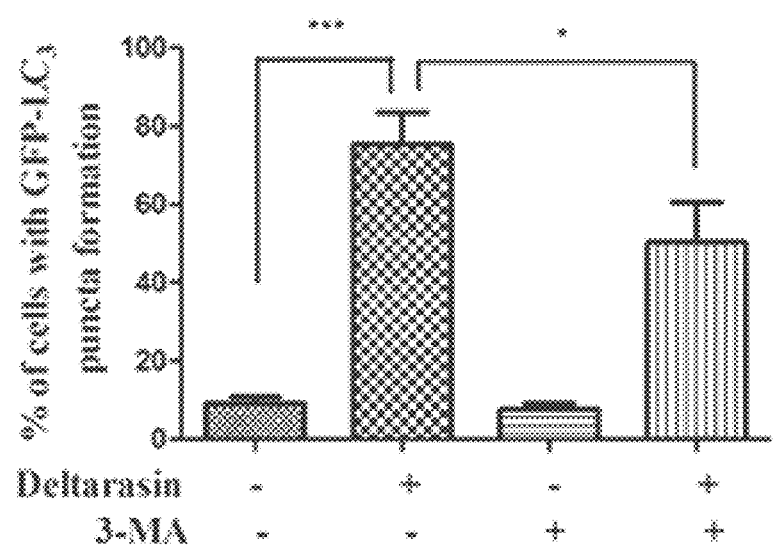

The conversion of soluble LC3-I to lipid bound LC3-II is associated with autophagosome formation which can be used as a marker for autophagy induction. As illustrated in FIG. 4A to 4C, treatment with deltarasin distinctly facilitated the conversion of LC3-I to LC3-II in PANC-1, A549 and H358 cells in a dose-dependent manner. In contrast, the accumulation of LC3-II induced by deltarasin could be suppressed in the presence of the direct autophagy inhibitor, 3-methyladenine (3-MA), a class III PI3K inhibitor in all three cancer cell lines (FIG. 4D to 4F). Similarly, the autophagy activity of deltarasin has been evaluated by transiently expressing the green fluorescent protein microtubule-associated protein light chain 3 (GFP-LC3) in A549 cells. As indicated in FIG. 4G to 4K, upon deltarasin treatment, increased percentage of GFP-LC3 puncta formation was observed in contrast to the untreated control cells, suggesting autophagosome formation was induced by deltarasin, while the number of GFP-LC3 puncta was significantly diminished in the presence of autophagy inhibitor 3-MA. Taken together, these data demonstrated for the first time that deltarasin induced autophagy in both pancreatic and lung cancer cells.

Example 5

Induction of Autophagy Through AMPK-mTOR Dependent Pathway by Deltarasin

Figure 5A:
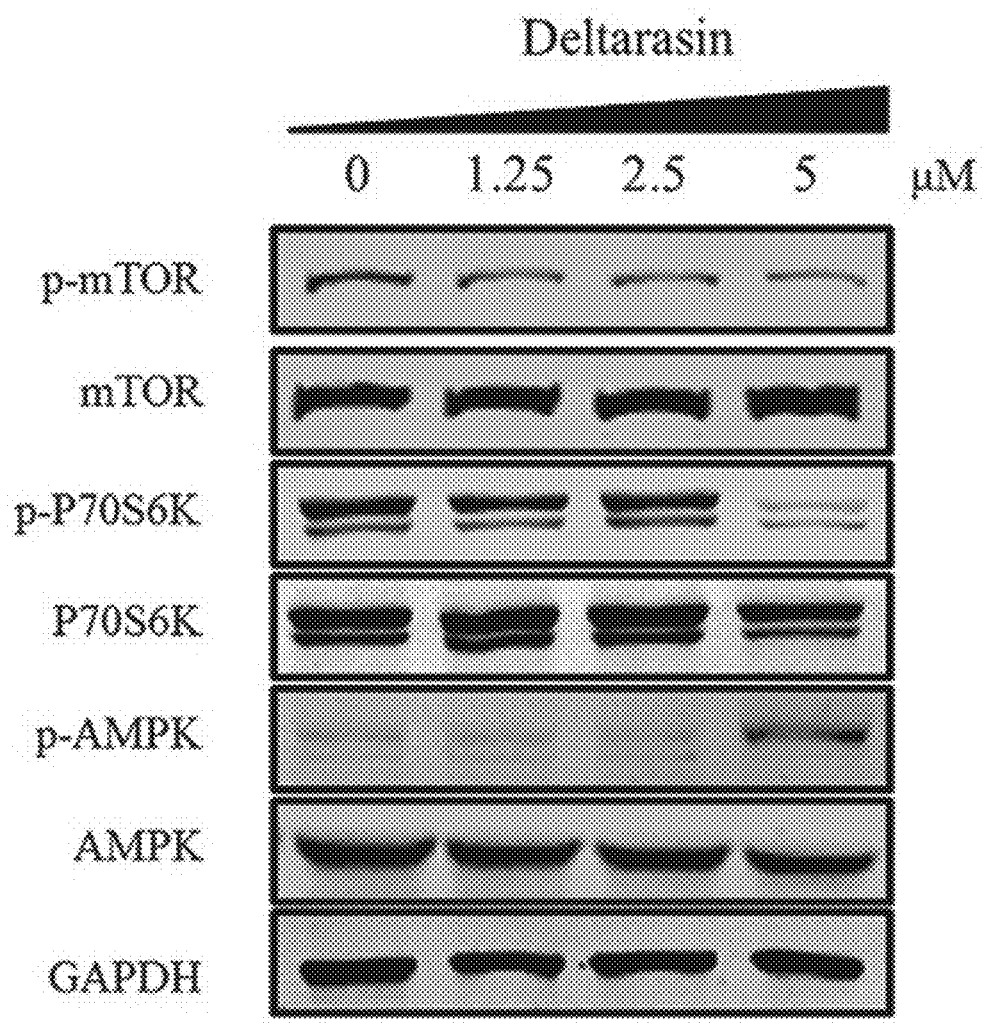
FIGS. 5A through 5C show that deltarasin induces autophagy through the activation of the AMPK-mTOR pathway in A549 cells.
Figure 5B:
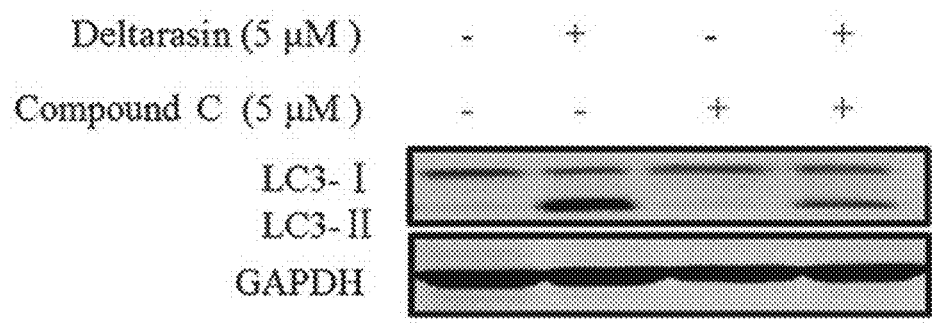
Figure 5C:
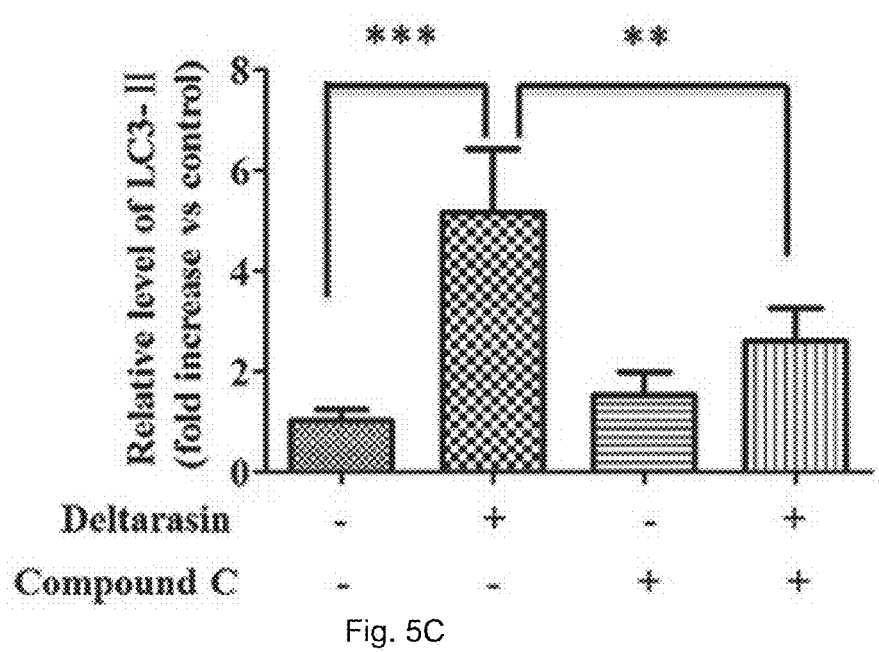

To further understand the mechanisms of deltarasin-induced autophagy, the possible involvement of AMP activated protein kinase (AMPK)-mammalian target of rapamycin (mTOR) signaling pathway has been evaluated. mTOR, which is a member of the phosphatidylinositol 3-kinase (PI3K) cell survival pathway, plays an important role in the regulation of cell growth and proliferation by monitoring nutrient availability, cellular energy levels, oxygen levels, and mitogenic signals. AMPK, which is a key energy sensor and regulates cellular metabolism to maintain energy homeostasis, can promote autophagy. It was further reported that mTOR is a sensor of changes in the cellular energy state via AMPK. Activation of this protein kinase inhibits mTOR-dependent signaling and inhibits protein synthesis. As shown in FIG. 5A, treatment of A549 with deltarasin suppressed mTOR and p70S6K phosphorylation with concomitant up-regulation of p-AMPK. In addition, accumulation of LC3-II was suppressed when deltarasin was used in combination with AMPK inhibitor compound C (FIGS. 5B and 5C). Taken together, the results suggest that deltarasin-induced autophagy in A549 cells is mediated through the activation of the AMPK-mTOR signaling pathway.

Example 6

Figure 6A:
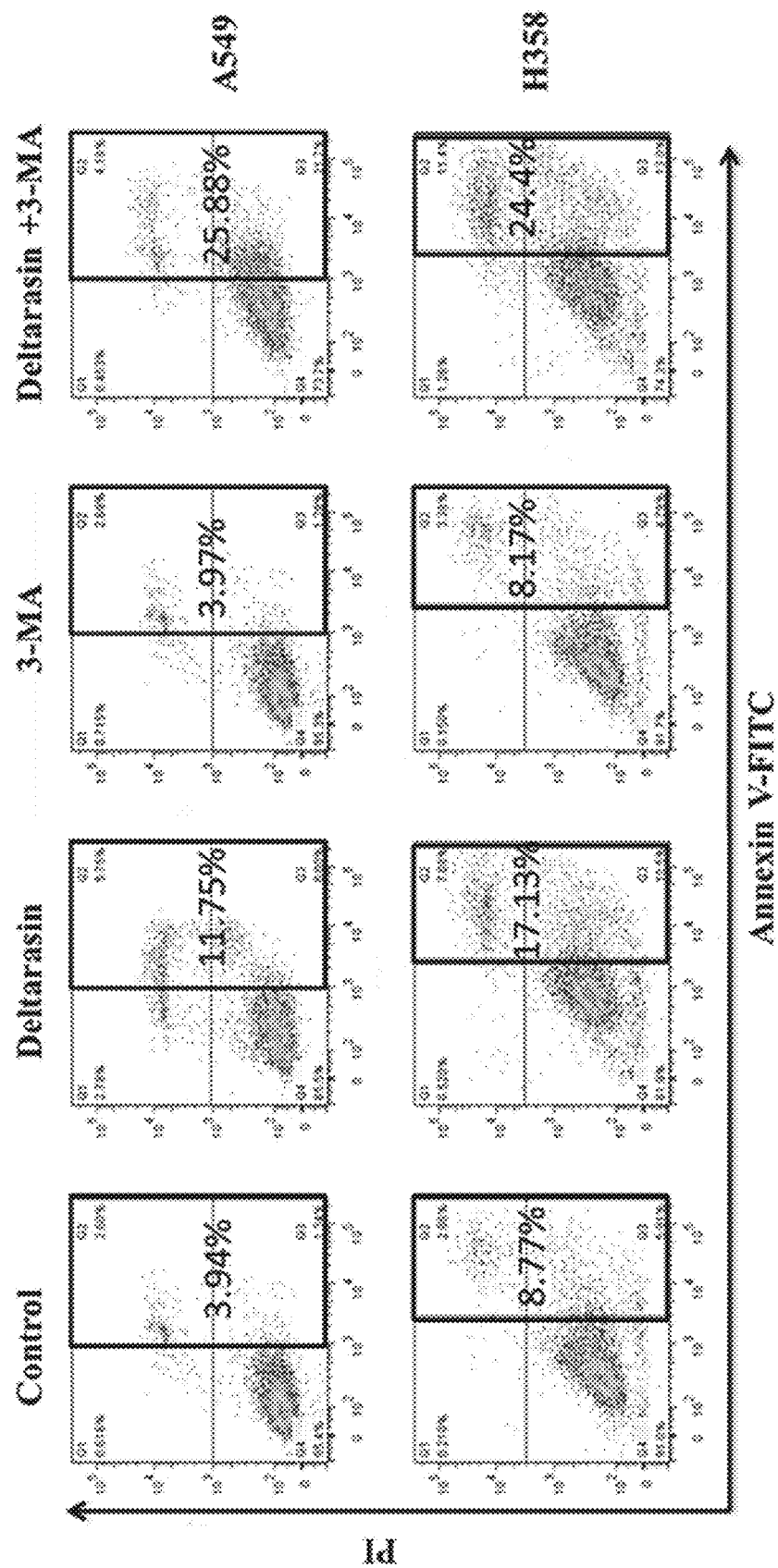
FIGS. 6A through 6G refer to the inhibition of autophagy with a direct autophagy inhibitor showing that the direct autophagy inhibitor enhances the anti-cancer effect of deltarasin in KRAS-positive NSCLC cells.
Figure 6B:
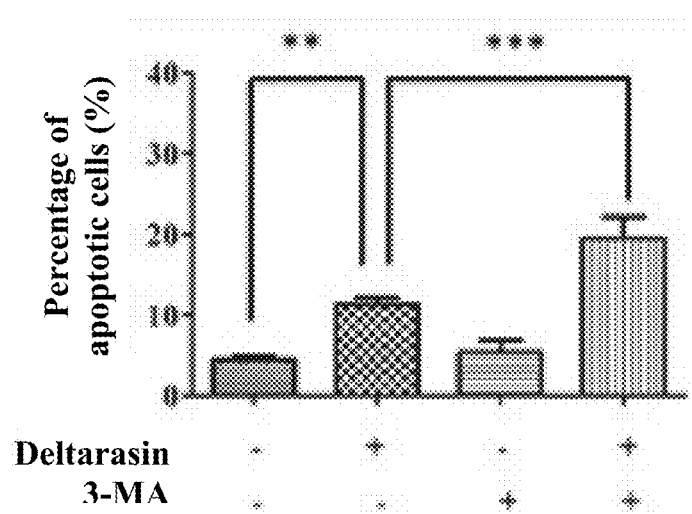
Figure 6C:
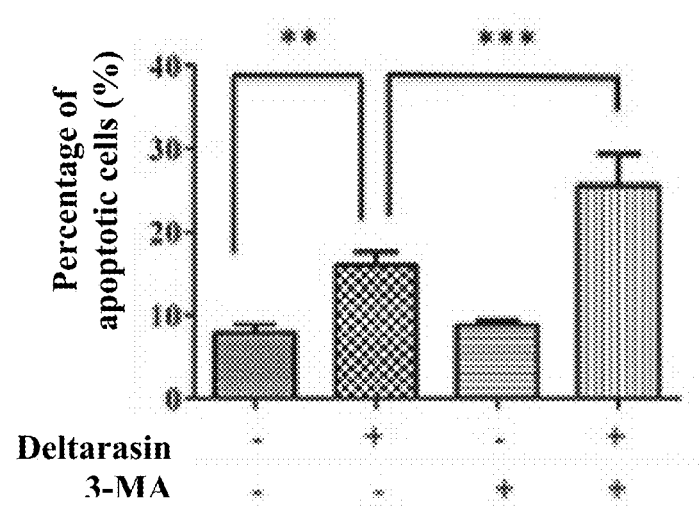

Inhibition of Deltarasin-Induced Autophagy and Effects on Cell Death of NSCLC Cells by Combining Deltarasin with 3-MA Low levels of autophagy may protect cells from stress and cell death, and autophagy induction promotes tumor resistance to chemotherapy. Thus, autophagy inhibition could be used in combination with chemotherapy to increase the sensitivity of cancer cells to drugs. Therefore, the mechanism of deltarasin-induced autophagy on both A549 and H358 cells and the role of autophagy on deltarasin sensitivity has been evaluated. As shown in FIG. 6A to 6C, treatment of A549 and H358 cells with 5 µM deltarasin for 24 hours induced 11.25% and 15.99% of cell apoptosis respectively, however, when cells were co-treated with deltarasin and 3-MA, it resulted in 21.7% and 25.54% of cell apoptosis respectively, suggesting that deltarasin-induced autophagy is tumor-protective which can be blocked in order to enhance the anti-cancer effect of deltarasin with 3-MA.

Figure 6D:
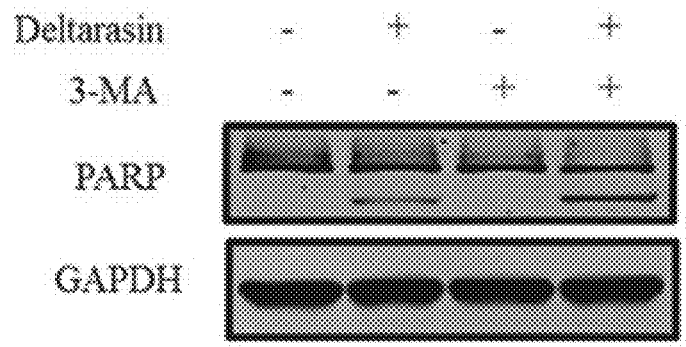
Figure 6E:
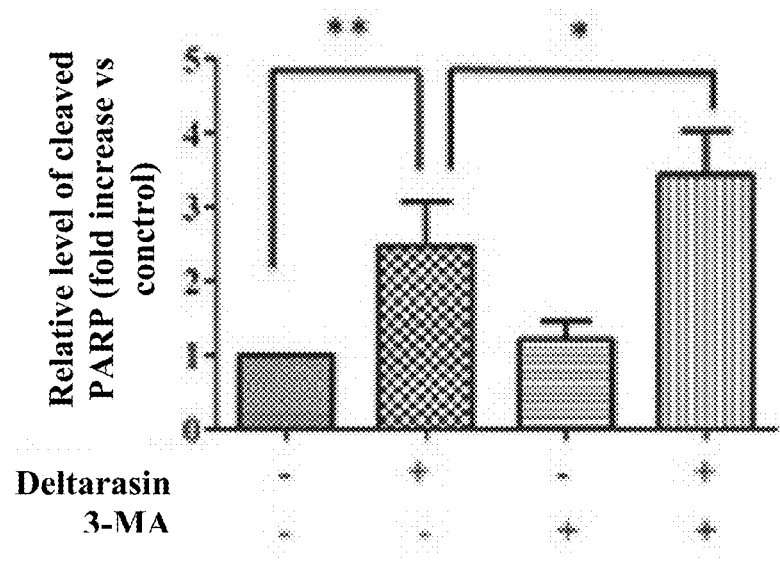
Figure 6F:
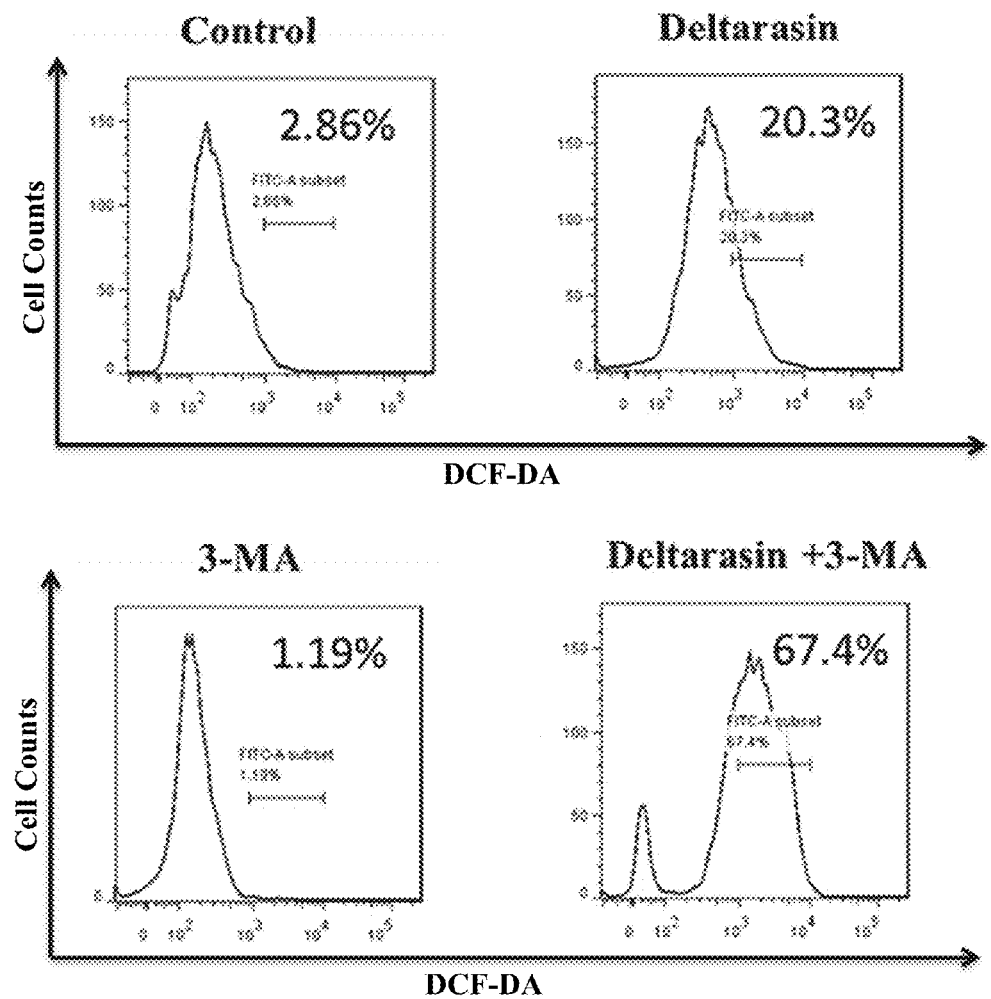
Figure 6G:
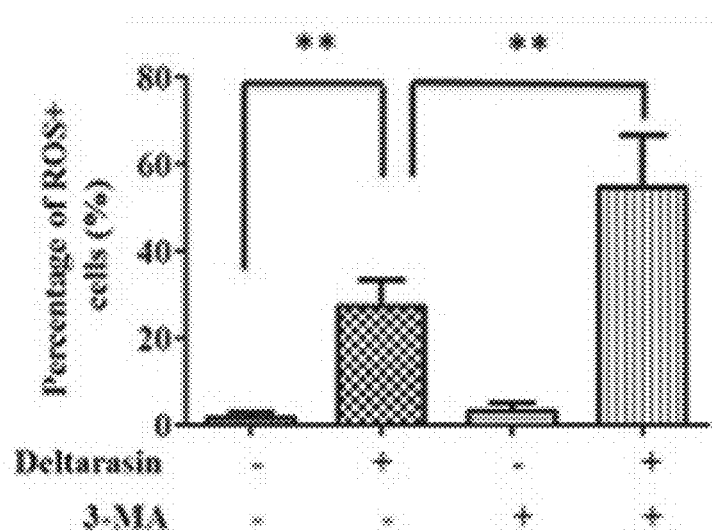

Moreover, the inhibition of autophagy further promoted the cleavage of PARP when compared with the deltarasin alone treatment group (FIGS. 6D and 6E). In addition, as shown by the enhanced levels of DCF-DA staining, a measure of ROS production, inhibition of autophagy further increased ROS generation (FIGS. 6F and 6G) leading to further cell damage, suggesting that deltarasin evoked protective autophagy. Taken together, these data prove that inhibition of deltarasin-induced autophagy potentiates apoptosis of A549 cells.

Example 7

Blocking Deltarasin-Induced ROS Suppresses Autophagy and Apoptosis

The role of ROS in cancer is controversial: low levels of ROS can support growth of cancer, however, high levels of ROS can trigger oxidative stress and protein damage of cancer cells, resulting in apoptosis (DeNicola, G. M., et al. Nature, 2011, 475(7354):106-109, Leung, E. L., et al. Antioxidants & redox signaling, 2016, 24(5):263-279). Similarly, autophagy was reported to have dual roles in cancer regulation, and it was reported that ROS can induce autophagy (Chen, N., et al., International journal of biological sciences, 2015, 11(7):833-844), therefore, it has been further examined whether deltarasin-induced autophagy is dependent on ROS generation in pancreatic and lung cancer cells, and further the role of ROS in deltarasin-induced apoptosis and autophagy has been evaluated. As shown in FIG. 7A to 7D, deltarasin significantly elevated intracellular ROS levels, whereas a general ROS scavenger, N-acetyl cysteine (NAC), suppressed the high level of ROS induced by deltarasin in all three cancer cell lines.

Figure 7A:
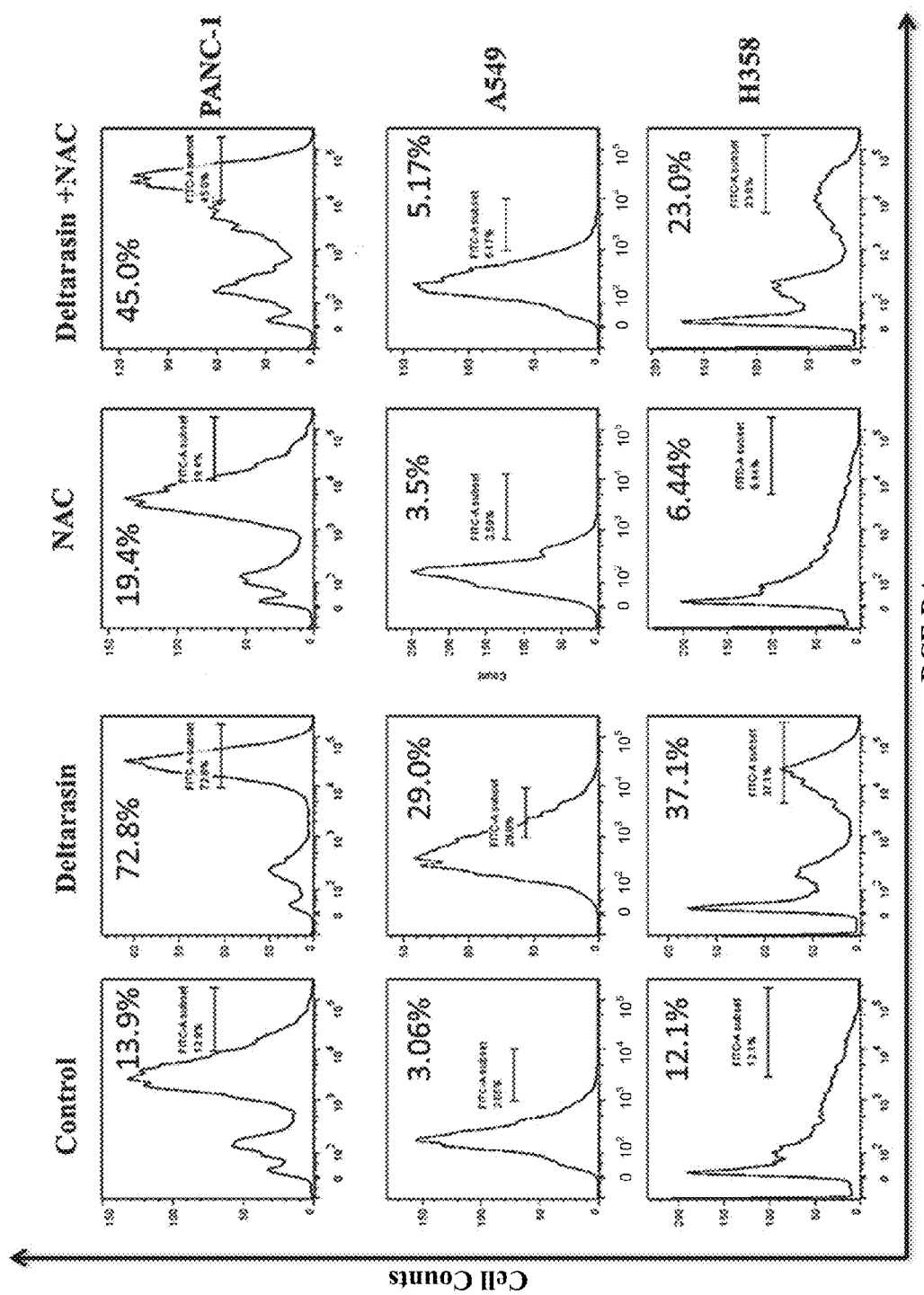
FIGS. 7A through 7H refer to the accumulation of ROS and shows that NAC reverses deltarasin-induced apoptosis.
Figure 7B:
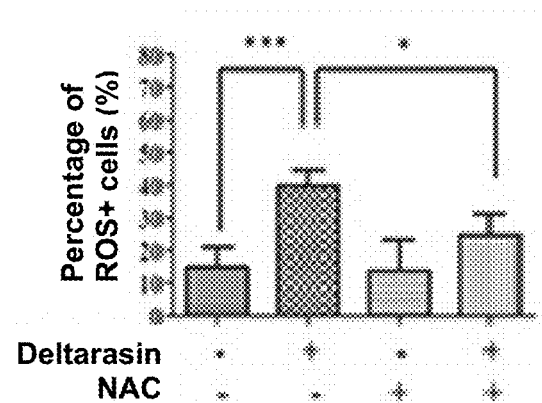
Figure 7C:
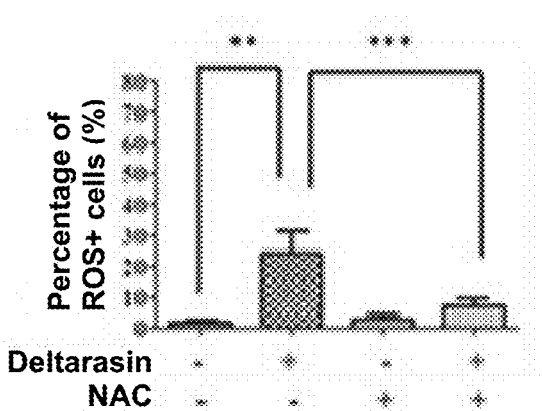
Figure 7D:
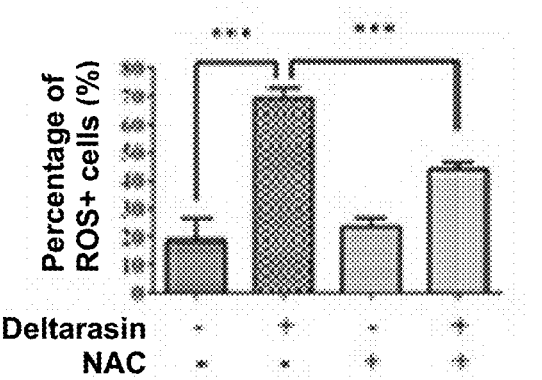
Figure 7E:
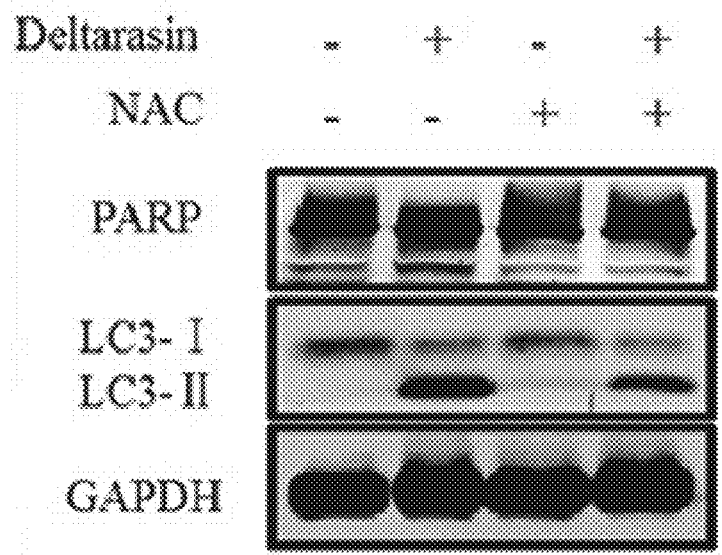
Figure 7F:
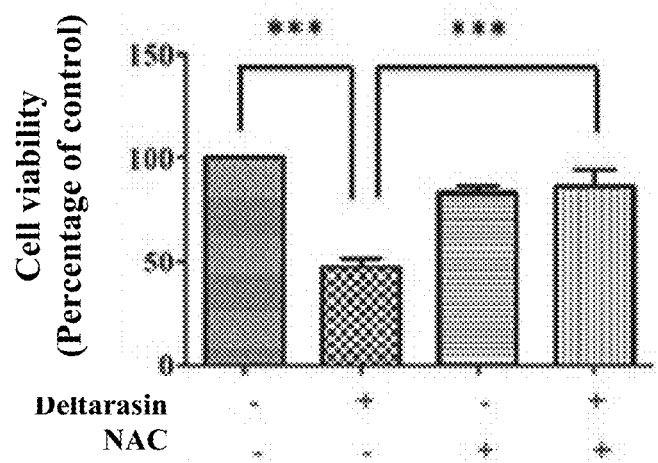
Figure 7G:
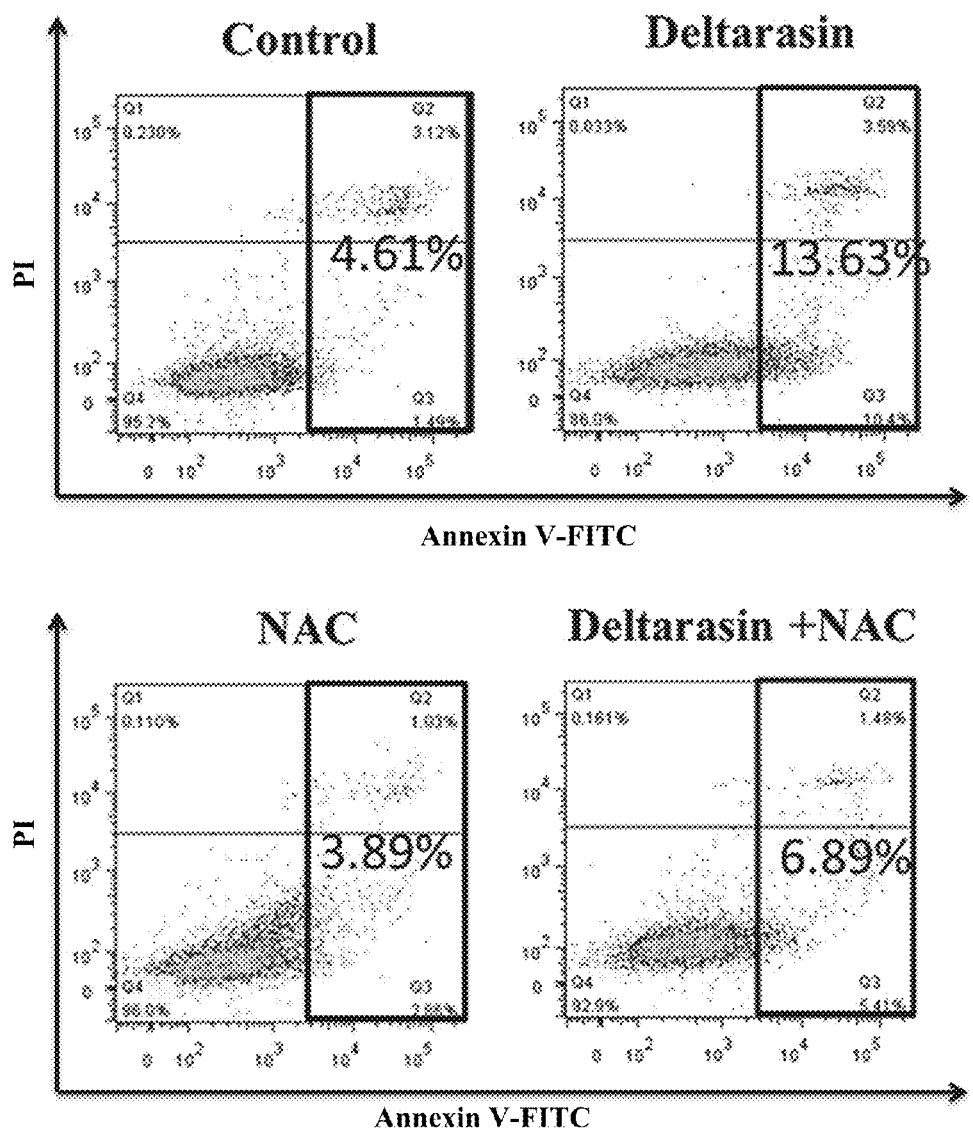
Figure 7H:
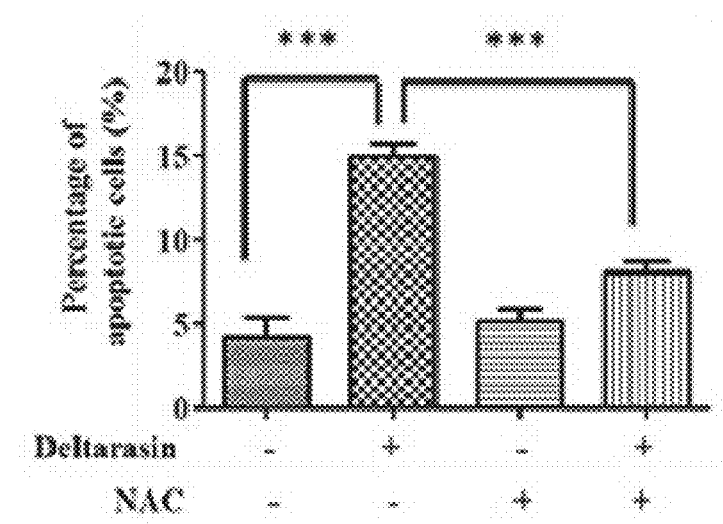
Figure 8A:
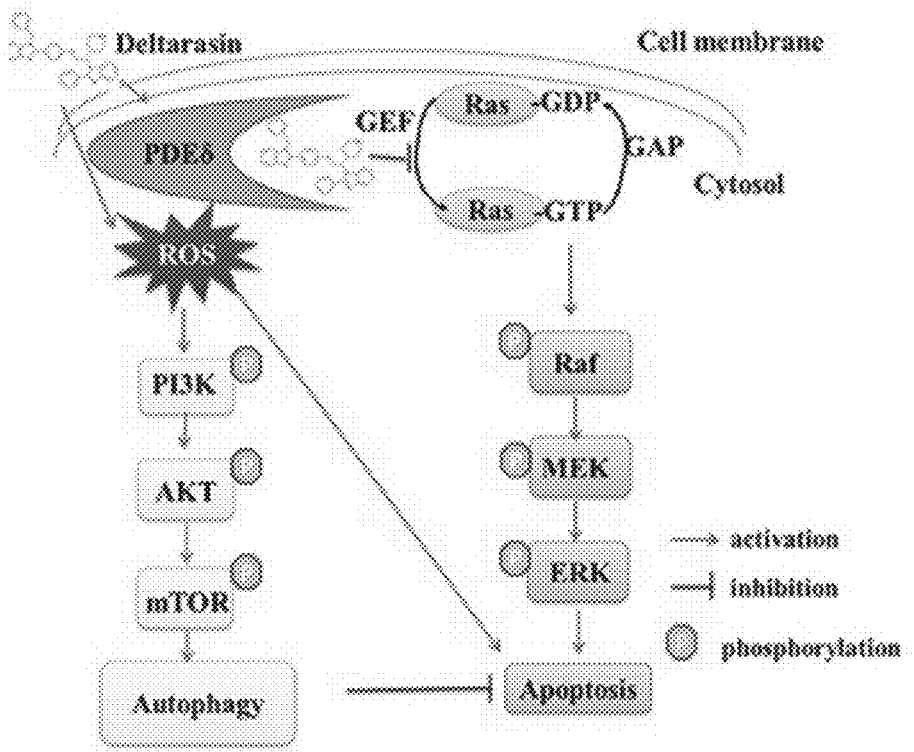
FIGS. 8A and 8B are schematic representations and might illustrate a mechanism the inventors assume to enhance deltarasin-induced apoptosis by blocking "tumor protective" autophagy with a direct autophagy inhibitor, in particular 3-MA in KRAS-positive cancer cells.
Figure 8B:
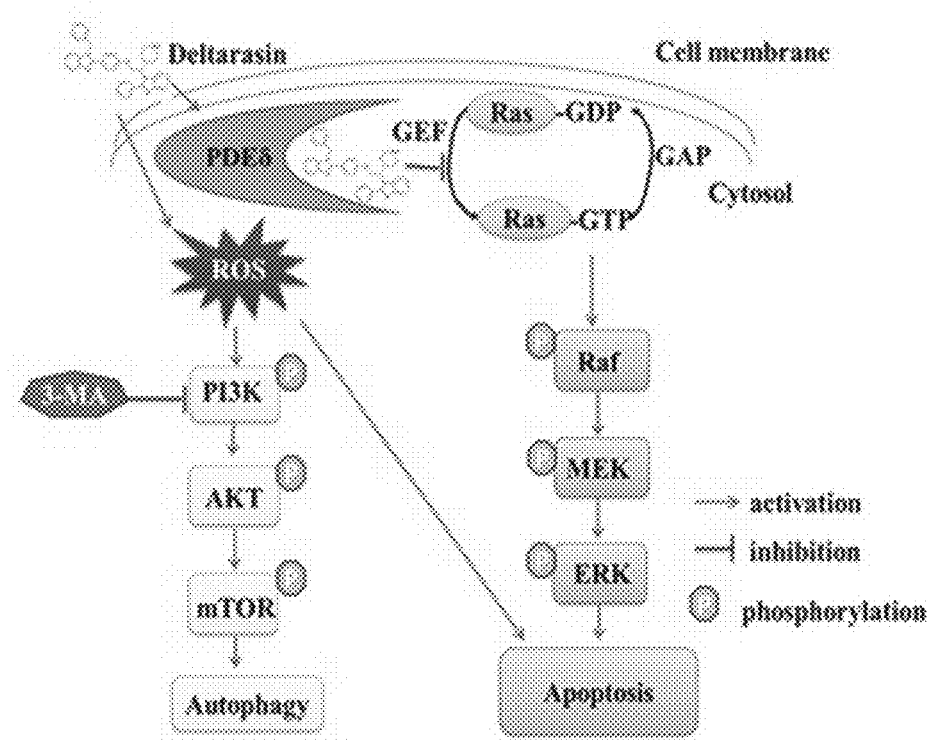

Notably, scavenging ROS with NAC suppressed both PARP cleavage and the accumulation of LC3-II in A549 cells blocking autophagy (FIG. 7E). However, flow cytometry analysis showed that co-treatment with NAC decreases deltarasin-induced cell cytotoxicity and apoptosis in A549 cells (FIG. 7F to 7H). All these data suggest that although there is a beneficial anti-cancer effect of blocking autophagy of deltarasin, simultaneously blocking ROS will weaken its beneficial effect due to a suppression of its oxidative damage to cancer cells. Using a direct autophagy inhibitor (e.g. 3MA) rather than an antioxidant (e.g. NAC) is thus a highly promising approach for potentiating the apoptotic activity of deltarasin in the future clinical application.

The invention claimed is:
1. A method of treating a subject suffering from a RAS-positive disease comprising administering an effective amount of a combination of:
(i) a PDEδ inhibitor having a structure of Formula (I),

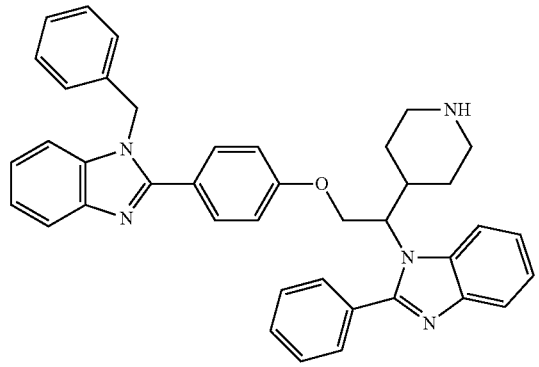

Formula (I)

and
(ii) a direct autophagy inhibitor
to the subject.
2. The method of claim 1, wherein the PDEδ inhibitor is deltarasin having a structure of Formula (Ia):

Formula (Ia)

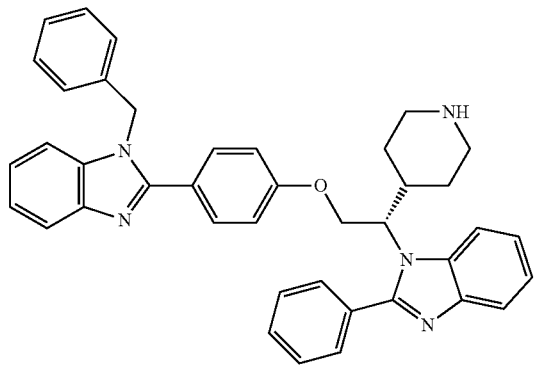

3. The method of claim 1, wherein the direct autophagy inhibitor is an inhibitor of class III phosphoinositide 3-kinase.

4. The method of claim 3, wherein the direct autophagy inhibitor is 3-methyladenine having a structure of Formula (II):

Formula (II)

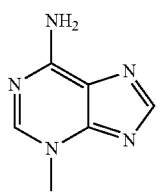

5. The method of claim 1, wherein the disease is cancer and the administration induces apoptosis of the cancer cells of said cancer.

6. The method of claim 1, wherein the disease is a KRAS-positive cancer.

7. The method of claim 1, wherein the disease is a KRAS-positive lung cancer or a KRAS-positive pancreatic cancer.

8. The method of claim 1, wherein the subject is a human and wherein the disease is a KRAS-positive non-small cell lung cancer having cancer cells with at least one KRAS gene mutation selected from one or more of G12C, G12A, G12D, G12S or G12V.

9. The method of claim 1, wherein a combination of at least 2.5 µM of the PDEδ inhibitor and at least 2.5 mM of the direct autophagy inhibitor is administered to the subject, and the administration of the combination of the direct autophagy inhibitor and the PDEδ inhibitor is associated with:

(i) a potentiated apoptotic activity of the PDEδ inhibitor; and (ii) a decreased autophagic activity of the PDEδ inhibitor.

10. The method of claim 1, wherein the PDEδ inhibitor and the direct autophagy inhibitor are administered simultaneously.

11. A method of potentiating the apoptotic activity of a PDEδ inhibitor in RAS-positive cells comprising contacting the cells with:

(i) the PDEδ inhibitor having a structure of Formula (I),

Formula (I)

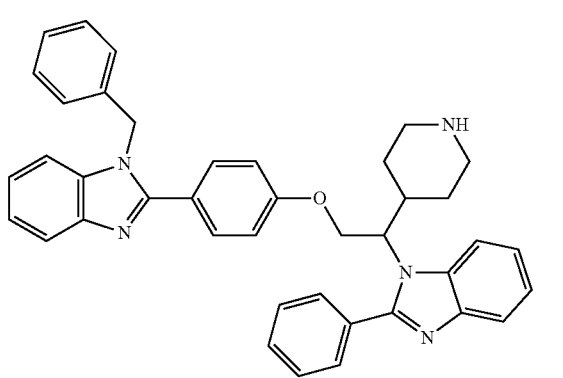

and (ii) a direct autophagy inhibitor.

12. The method of claim 11, wherein the RAS-positive cells are contacted with a concentration of at least 2.5 mM of the direct autophagy inhibitor which increases the percentage of apoptotic cells and the cleavage of poly (ADP-ribose) polymerase and/or the reactive oxygen species production as present when the RAS-positive cells are contacted with the same concentration of the PDEδ inhibitor.

13. The method of claim 11, wherein the RAS-positive cells are contacted with a concentration of at least 2.5 mM of the direct autophagy inhibitor which decreases the autophagic activity of the PDEδ inhibitor.

14. The method of claim 11, wherein the PDEδ inhibitor is deltarasin having a structure of Formula (Ia):

Formula (Ia)

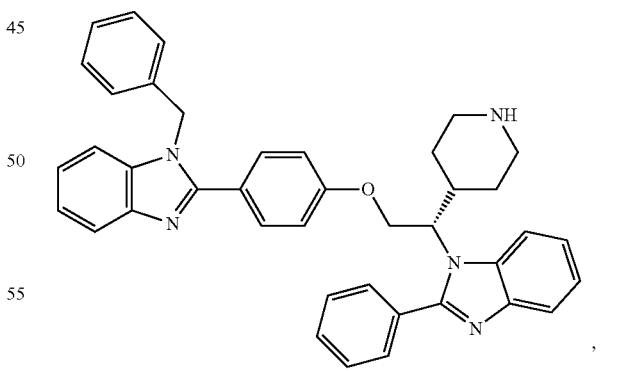

the direct autophagy inhibitor is an inhibitor of class III phosphoinositide 3-kinase and the RAS-positive cells are RAS-positive cancer cells.

15. The method of claim 14, wherein the direct autophagy inhibitor is 3-methyladenine having a structure of Formula (II):

Formula (II)

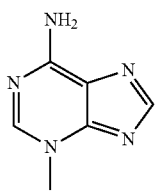

16. The method of claim 11, wherein the RAS-positive cells are contacted with the PDEδ inhibitor and the direct autophagy inhibitor simultaneously.

17. The method of claim 11, wherein the RAS-positive cells are contacted with a concentration of about 5 μM of the PDEδ inhibitor and about 5 mM of the direct autophagy inhibitor for at least 24 h and wherein the PDEδ inhibitor is deltarasin having a structure of Formula (Ia):

Formula (Ia)

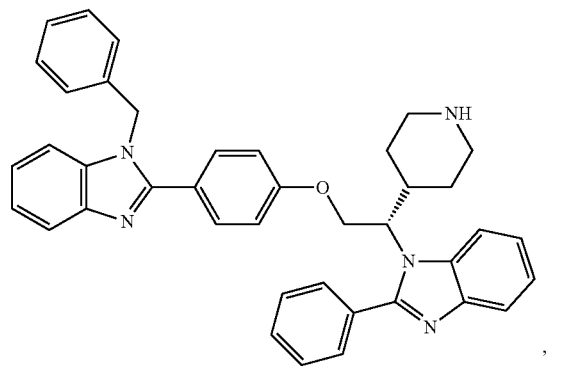

and the direct autophagy inhibitor is 3-methyladenine having a structure of Formula (II):

Formula (II)

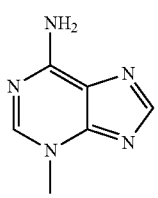

18. A method of treating a subject suffering from a RAS-positive lung cancer comprising administering an effective amount of a pharmaceutical composition comprising a PDEδ inhibitor having a structure of Formula (I):

Formula (I)

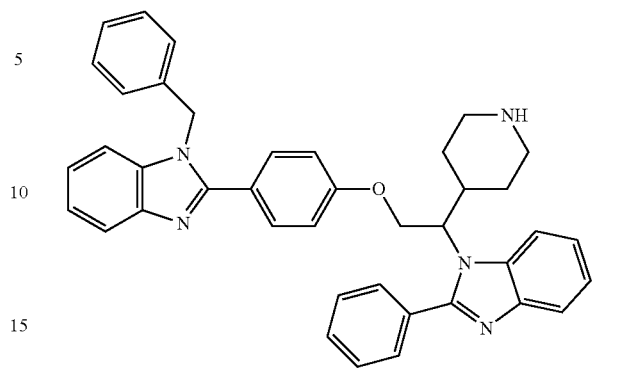

and a direct autophagy inhibitor to the subject.

19. The method of claim 18, wherein the PDEδ inhibitor is deltarasin having a structure of Formula (Ia):

Formula (Ia)

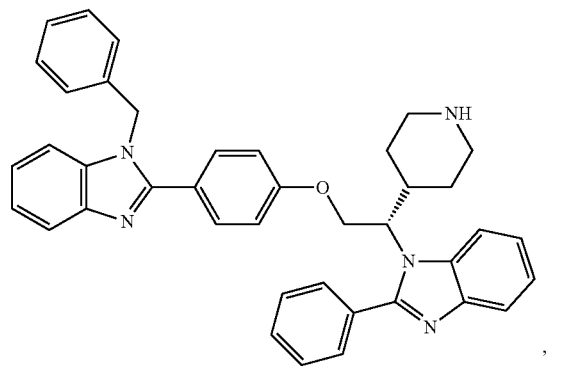

and the direct autophagy inhibitor is 3-methyladenine having a structure of Formula (II):

Formula (II)

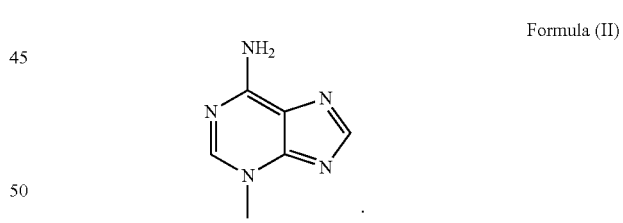

20. The method of claim 18, wherein the RAS-positive lung cancer is a KRAS-positive non-small cell lung cancer adenocarcinoma.

* * * * *